(12) United States Patent
Siripragada et al.

(10) Patent No.: US 7,223,881 B2
(45) Date of Patent: May 29, 2007

(54) PROCESS FOR THE PREPARATION OF NEW ANTIDIABETIC AGENTS

(75) Inventors: Mahender Rao Siripragada, Hyderabad (IN); Prabhakar Chebiyyam, Hyderabad (IN); Rajender Kumar Potlapally, Hyderabad (IN); Chandra Sekhar Batchu, Hyderabad (IN); Ramabhadra Sarma Mamillapalli, Hyderabad (IN); Om Reddy Gaddam, Hyderabad (IN)

(73) Assignee: Dr. Reddy's Laboratories Limited, Hyderabad (IN)

( * ) Notice: Subject to any disclaimer, the term of this patent is extended or adjusted under 35 U.S.C. 154(b) by 148 days.

(21) Appl. No.: 10/325,176

(22) Filed: Dec. 20, 2002

(65) Prior Publication Data

US 2003/0125553 A1   Jul. 3, 2003

(30) Foreign Application Priority Data

Oct. 29, 1998   (IN) .................. 2433/MAS/1998

(51) Int. Cl.
C07C 69/76   (2006.01)
(52) U.S. Cl. .......................................... 560/8
(58) Field of Classification Search .............. 560/8
See application file for complete search history.

(56) References Cited

U.S. PATENT DOCUMENTS 5,391,565 A * 2/1995 Hindley .................. 514/375
6,054,453 A * 4/2000 Lohray et al. ........... 514/226.2

FOREIGN PATENT DOCUMENTS

| HU | P9700264 | 10/1997 |
|---|---|---|
| WO | 9517394 | 6/1995 |
| WO | 9604260 | 2/1996 |
| WO | 9741097 | 11/1997 |
| WO | WO 99/19313 | 4/1999 |
| WO | 0140159 | 6/2001 |
| WO | 0140165 | 6/2001 |
| WO | 0140166 | 6/2001 |
| WO | 0140169 | 6/2001 |
| WO | 0140170 | 6/2001 |
| WO | 0140171 | 6/2001 |
| WO | 0140172 | 6/2001 |
| WO | 0153257 | 7/2001 |

OTHER PUBLICATIONS

English Abstract of P9700264 dated Oct. 28, 1997.

* cited by examiner

*Primary Examiner*—Alton Pryor
(74) *Attorney, Agent, or Firm*—Ladas and Parry LLP

(57) ABSTRACT

The present invention relates to an improved process for the preparation of novel antidiabetic compounds having formula (1) where $R^1$ represents hydrogen or lower alkyl group and X represents hydrogen or halogen atom

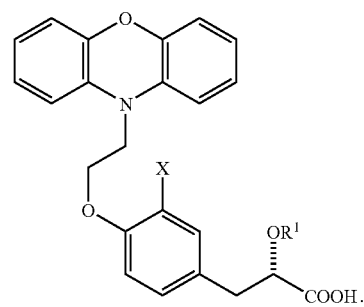

(1)

3 Claims, No Drawings

PROCESS FOR THE PREPARATION OF NEW ANTIDIABETIC AGENTS

FIELD OF THE INVENTION

The present invention relates to an improved process for the preparation of novel antidiabetic compounds having the formula (1).

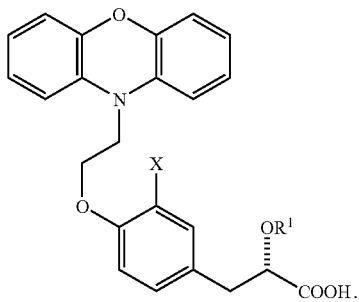

(1)

where $R^1$ represents hydrogen or lower alkyl group, and X represents hydrogen or halogen atom.

U.S. patent application Ser. No. 09/012,585, describes a process for the preparation of a novel antidiabetic compound having the formula (1). The process described therein comprises converting aldehyde of formula (2) where X is as defined above to a compound of formula (3) where all symbols are as defined above and $R^2$ represents lower alkyl group, reducing the compound of formula (3) to produce a compound of formula (4), hydrolysing the compound of formula (4) to obtain an acid of formula (5), converting the acid of formula (5) to an amide of the formula (6) and hydrolysing the amide to produce the compound of formula (1), where X and $R^1$ are as defined above. The process is shown in the scheme-1 given below

OBJECTIVES OF THE PRESENT INVENTION

The main objective of the present invention is therefore to provide a convergent synthesis of the compounds of the formula (1).

Another objective of the present invention is to provide a convergent and stereoselective synthesis of the compounds of the formula (1) and a commercial viable process.

Another objective of the present invention is to provide a process for the preparation of the compounds of the formula (1) by preparing chiral amine addition salts followed by hydrolysis to afford the uni-isomer of an intermediate which can later be converted into the required isomers having the formula (1). In the event of a small amount of racemization, if any, during the course of converting the intermediate to the final compounds of the formula (1), resolution can easily be done by employing chiral amines without losing much of the compounds of the formula (1).

Accordingly, the present invention provides a process for the preparation of compounds of the formula (1) where $R^1$ represents hydrogen atom or lower alkyl group such as $C_1$–$C_6$ group preferably methyl, ethyl, propyl and the like, X represents hydrogen atom or halogen atom such as chlorine, bromine or iodine which comprises:

(i) benzylating p-hydroxybenzaldehyde of the formula (7) by conventional methods to yield a compound of the formula (8), (ii) reacting the compound of the formula (8) with alkyl haloacetates in the presence of a base at a temperature in the range of –10° C. to 60° C. (Darzen's condensation) to yield the glycedic ester of the formula (9) where R represents lower alkyl group, (iii) opening up the epoxide group of the glycedic ester of the compound of the formula (9) by conventional methods to yield a compound of the formula (10) where R is as defined above,

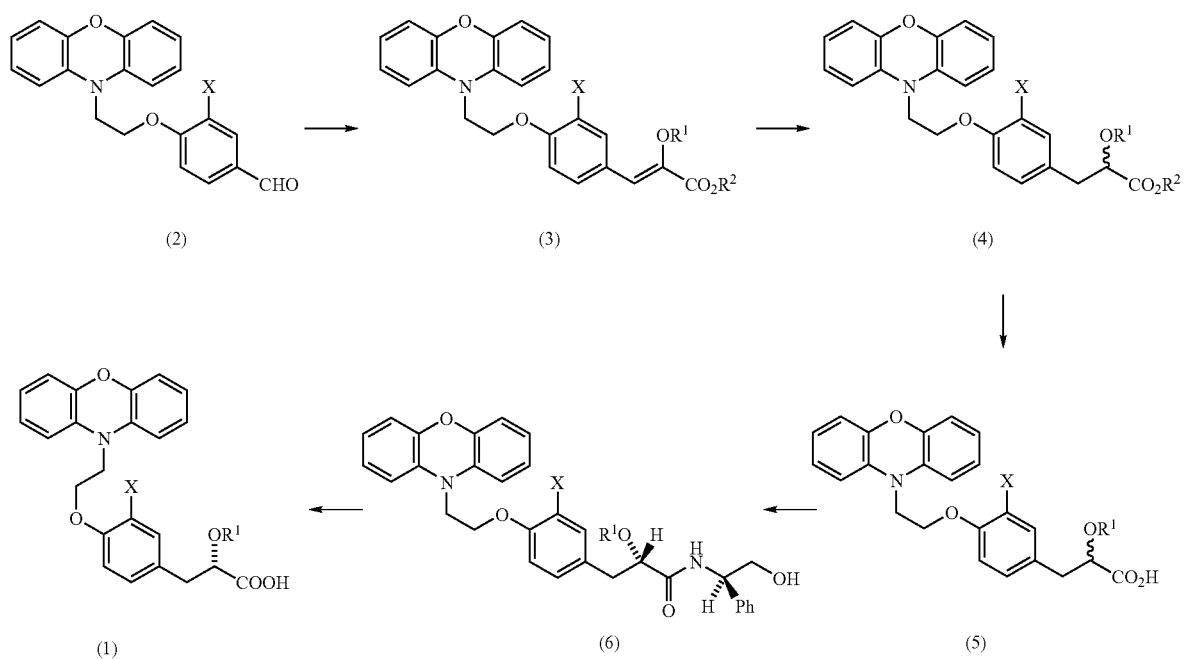

Scheme-1

(iv) hydrolyzing the compound of the formula (10) by conventional methods followed by the resolution of the resultant compound to yield (S)-hydroxy compound of the formula (11), (v) converting the compound of the formula (11) to the corresponding alkylated compound of the formula (12) where $R^1$ represents hydrogen or lower alkyl, $R^2$ represents lower alkyl group in one pot reaction by treating it with an alkylating agent in the presence of base, (vi) debenzylating the compound of the formula (12) by conventional methods to produce the compound of the formula (13) where $R^1$ and $R^2$ are as defined above, if desired, (vii) converting the compound of the formula (13) to a compound of formula (14) where X represents halogen atom and all other symbols are as defined above by conventional methods, (viii) reacting either the compound of the formula (13) or the compound of the formula (14) with phenoxazinyl mesylate of the formula (15) to give the ester of the formula (16) where X represents hydrogen or halogen atom, and $R^1$ and $R^2$ are as defined above, (ix) hydrolysing the compound of the formula (16) by conventional methods to yield the compound of the formula (1) defined above, and if desired, (x) chemically resolving the compound of formula (1) by employing chiral amines, in case there is any racemization during the course of converting the (S)-hydroxy compound of the formula (11) to the final compound of formula (1).

The process explained above is shown in scheme-2 below:

Benzyl protection of p-hydroxybenzaldehyde having the formula (7) affords the protected aldehyde of the formula (8). Reaction of the compound of the formula (8) with alkylhaloacetates such as methyl chloroacetate, methylbromoacetate, ethylchloroacetate, ethylbromoacetate, and the like in the presence of a base such as sodium methoxide, sodium ethoxide, sodium carbonate, potassium carbonate, potassium sec. Butoxide, t-BuOK and the like gives the glycedic ester of the formula (9) where R represents lower alkyl group such as $C_1$–$C_6$ alkyl preferably methyl, ethyl and the like. The glycedic ester of the formula (9) is opened up with reagents such as Raney. Ni, $H_2$/Pd—C, borane reagents, and the like to give the racemic hydroxy ester having the formula (10). Hydrolysis of the ester of the formula (10) followed by its resolution using chiral amines such as R(+)α-methylbenzylamine, S(+)-phenylglycinol, cinchonidine, ephedrine, n-octylglucosamine and the like gives the optically active hydroxy acid having the formula (11), which on alkylation using alkylating agents such as diethylsuphate, ethyliodide, methyliodide, dimethylsuphate and the like, in the presence of a base such as NaH, NaOH, KOH, t-BuOK, $K_2CO_3$, $NaHCO_3$, and the like, affords the compound of the formula (12) where $R^1$ represents hydrogen or lower alkyl group such as $C_1$–$C_6$ group preferably methyl, ethyl, propyl and the like, $R^2$ represents lower alkyl group such as $C_1$–$C_6$ group preferably methyl, ethyl, propyl and the like. The compound of the formula (12) upon deberizy-

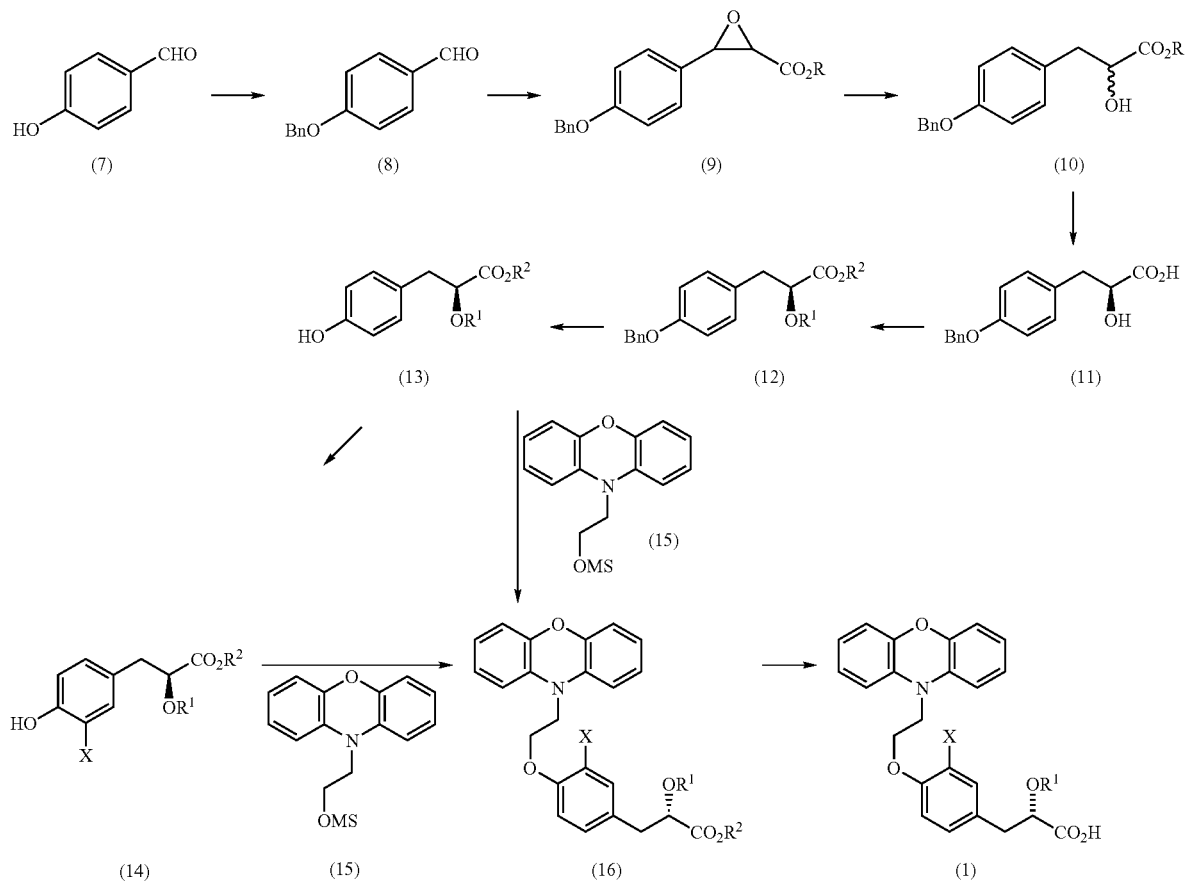

Scheme-2 lation using reagents such as $H_2/Pd$—C, HCl/AcOH, and the like in the presence of solvents such as THF, ethylacetate, 1,4-dioxane, AcOH and the like gives the substituted phenol of the formula (13). The compound of the formula (13) is converted to a compound of formula (14) using suitable halogenating agents such as ICl/HCl $I_2$/KI, $Cl_2/H^+$, $Br_2$/AcOH and the like. The optically active compound of the formula (13) or the compound of the formula (14) reacts with the phenoxazinyl mesylate having the formula (15) to give the ester of the formula (16) which on hydrolysis employing conventional methods yields the required compound of the formula (1) in an optically pure form. However, in the event of a small amount of racemization, if any, during the course of converting the intermediate of the formula (11) to the final compound of the formula (1), resolution can easily be done employing chiral amines such as those described above without losing much of the compound of the formula (1).

The present invention also provides another improved process for the preparation of compounds of the formula (1) described above which comprises:

(i) benzylating p-hydroxybenzaldehyde of the formula (7) by conventional methods to yield a compound of the formula (8), (ii) reacting the compound of the formula (8) with alkyl haloacetates in the presence of a base at a temperature in the range of −10° C. to 60° C. (Darzen's condensation) to yield the glycedic ester of the formula (9) where R represents lower alkyl group, (iii) opening up the epoxide group of the glycedic ester of the compound of the formula (9) by conventional methods to yield a compound of the formula (10) where R has the meaning given above, (iv) alkylating the compound of the formula (10) using alkylating agent in the presence of a base to obtain a compound of the formula (12a) where $R^1$ represents hydrogen or lower alkyl, $R^2$ represents lower alkyl group, (v) debenzylating the compound of the formula (12a) by conventional methods to produce the compound of the formula (13a) where $R^1$ and $R^2$ are as defined above, if desired, (vi) converting the compound of the formula (13a) to a compound of formula (14a) where X represents halogen atom $R^1$ and $R^2$ are as defined above by conventional methods, (vii) reacting either the compound of the formula (13a) or the compound of formula (14a) with phenoxazinyl mesylate of the formula (15) to give the ester of the formula (4) where X represents hydrogen or halogen atom, $R^1$ and $R^2$ are as defined above, (viii) hydrolysing the compound of the formula (4) by conventional methods to yield the racemic compound of the formula (5) where X represents hydrogen or halogen atom, $R^1$ and $R^2$ are as defined above, and (ix) chemically resolving the compound of formula (5) by employing chiral amines, to the final compound of formula (1) optionally through an intermediate amide of the formula (6) where X represents hydrogen or halogen atom and $R^1$ are as defined above.

The process explained above is shown in scheme-3 below:

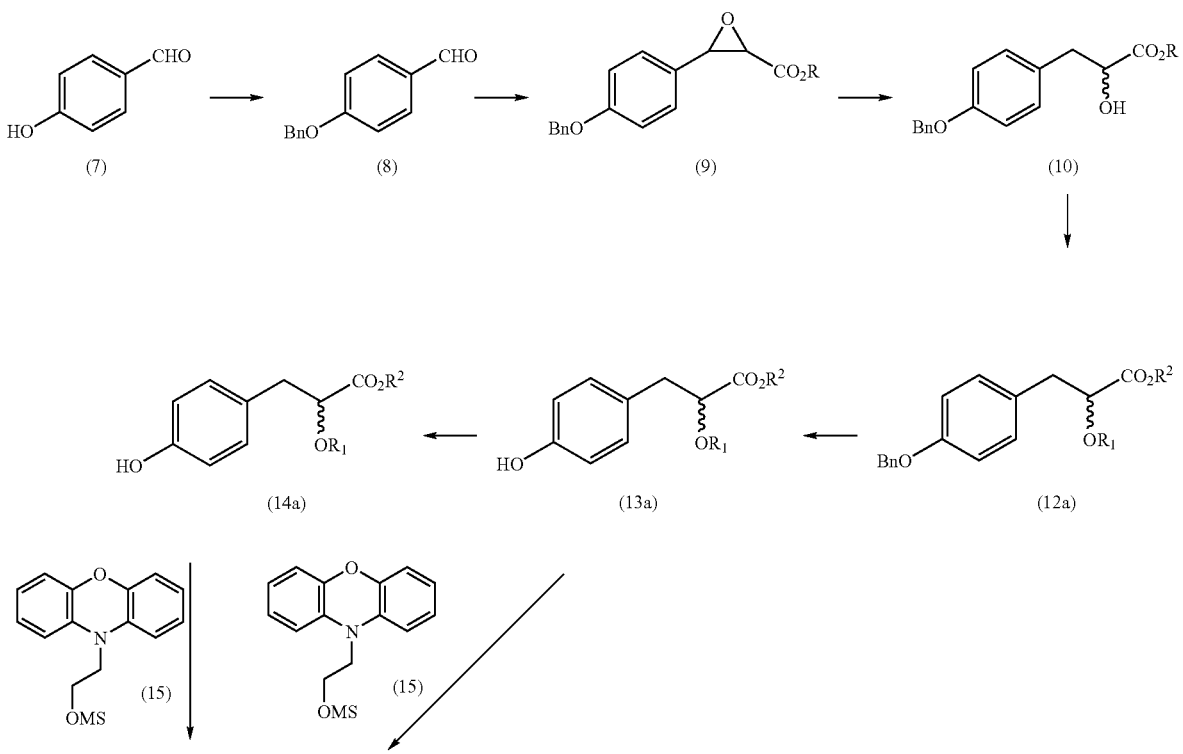

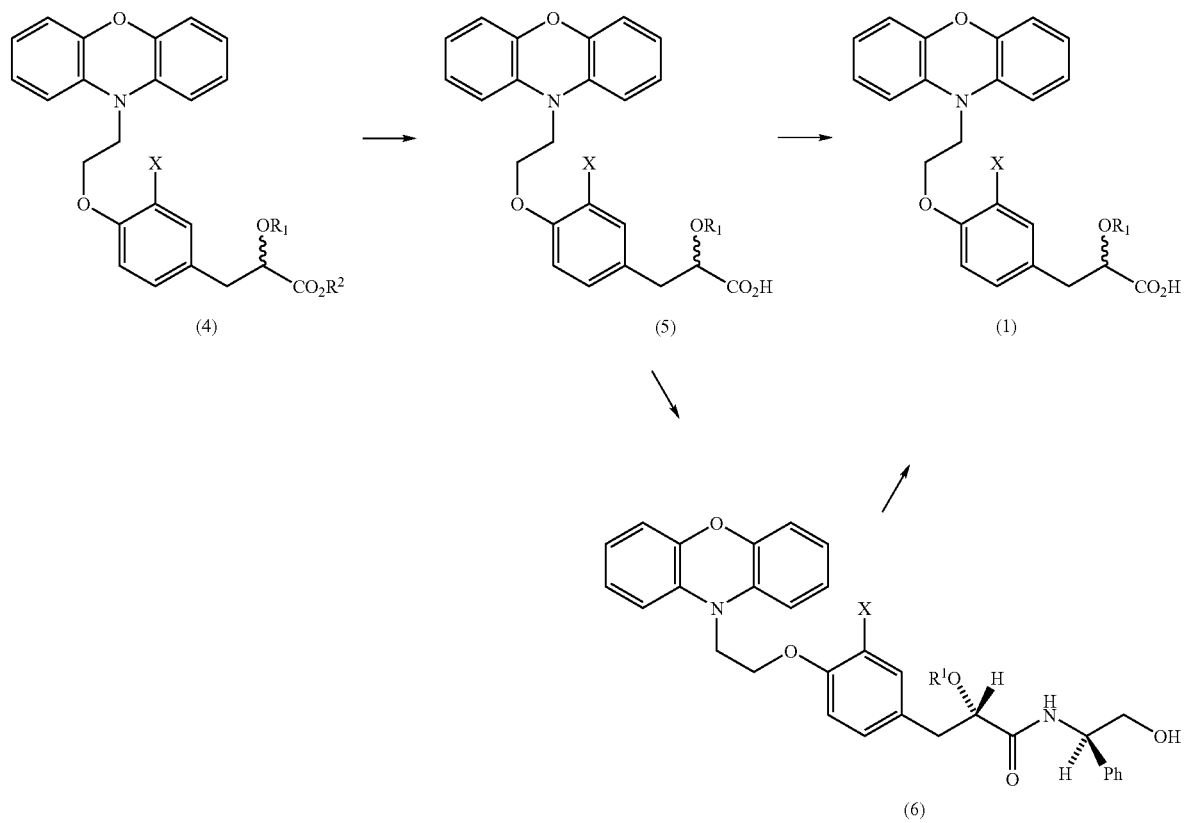

Benzyl protection of p-hydroxybenzaldehyde having the formula (7) affords the protected aldehyde of the formula (8). Reaction of the compound of the formula (8) with alkylhaloacetates such as methylchloroacetate, methylbromoacetate, ethylchloroacetate, ethylbromoacetate, and the like in the presence of a base such as sodium methoxide, sodium ethoxide, sodium carbonate, potassium carbonate, potassium sec. Butoxide, t-BuOK and the like gives the glycedic ester of the formula (9) where R represents lower alkyl group such as $C_1$–$C_6$ group, preferably methyl, ethyl, and the like. The glycedic ester of the formula (9) is opened up with reagents such as Raney. Ni, $H_2$/Pd—C, borane reagents, and the like to give the racemic hydroxy ester having the formula (10), which on alkylation using alkylating agents such as diethylsuphate, ethyliodide, methyliodide, dimethylsuphate and the like, in the presence of a base such as NaH, NaOH, KOH, t-BuOK, $K_2CO_3$, $NaHCO_3$ and the like affords the compound of the formula (12a) where $R^1$ represents hydrogen or lower alkyl group such as $C_1$–$C_6$ group preferably methyl, ethyl, propyl and the like, $R^2$ represents lower alkyl group such as $C_1$–$C_6$ group, preferably methyl, ethyl, propyl and the like. The ethoxy ester of the formula (12a) upon debenzylation using reagents such as $H_2$/Pd—C, HCl/AcOH, and the like in the presence of solvents such as THF, ethyl acetate, 1,4-dioxane, AcOH and the like gives the substituted phenol of the formula (13a). The compound of the formula (13a) is converted to a compound of formula (14a) using suitable halogenating agents such as ICl/HCl, $I_2$/KI, $Cl_2$/$H^+$, $Br_2$/AcOH and the like. The compound of the formula (13a) or the compound of formula (14a) reacts with the phenoxazinyl mesylate having the formula (15) to give the ester of the formula (4) which on hydrolysis employing conventional methods gives racemic acid of the formula (5). The racemic acid on resolution using chiral amines such as R(+)α-methylbenzylamine, S(+)-phenylglycinol, cinchonidine, ephedrine, n-octylglucosamine and the like, yields the required compound of the formula (1) in an optically pure form optionally through an intermediate amide of the formula (6).

The present invention also provides yet another improved process for the preparation of compound of the formula (1) described above which comprises:

(i) reacting p-hydroxybenzaldehyde of the formula (7) with hydantoin of the formula (17) by conventional methods to yield a compound of the formula (18), (ii) hydrolysing the compound of the formula (18) by conventional methods to yield a compound of the formula (19).

(iii) reducing the compound of the formula (19) by conventional methods to yield a compound of the formula (20), where R represents hydrogen or lower alkyl croup, (iv) benzylating the compound of the formula (20) by conventional methods to yield a compound of the formula (10) where R has the meaning given above, (v) hydrolysing the compound of the formula (10) by conventional methods followed by resolution to yield (S)-hydroxy compound of the formula (11), (vi) converting the compound of the formula (11) to the corresponding alkylated compound of the formula (12) where $R^1$ represents hydrogen or lower alkyl group, $R^2$ represents lower alkyl group in one pot reaction by treating it with an alkylating agent in the presence of a base, (vii) debenzylating the compound of the formula (12) by conventional methods to produce the compound of formula (13), (viii) if desired, converting the compound of formula (13) to a compound of formula (14) where X represents halogen atom, $R^1$ and $R^2$ are as defined above, by conventional methods, (ix) reacting either the compound of formula (13) or the compound of formula (14) with phenoxazinyl mesylate of the formula (15) to give the ester of the formula (16) where X represents hydrogen or halogen atom, $R^1$ and $R^2$ are as defined above, (x) hydrolysing the compound of the formula (16) by conventional methods to yield the compound of the formula (1) defined above, and if desired, (xi) chemically resolving the compound of formula (1) by employing chiral amines, in case there is any racemization during the course of converting the (S)-hydroxy compound of the formula (11) to the final compound of formula (1).

The process described above is as shown in scheme-4 below:

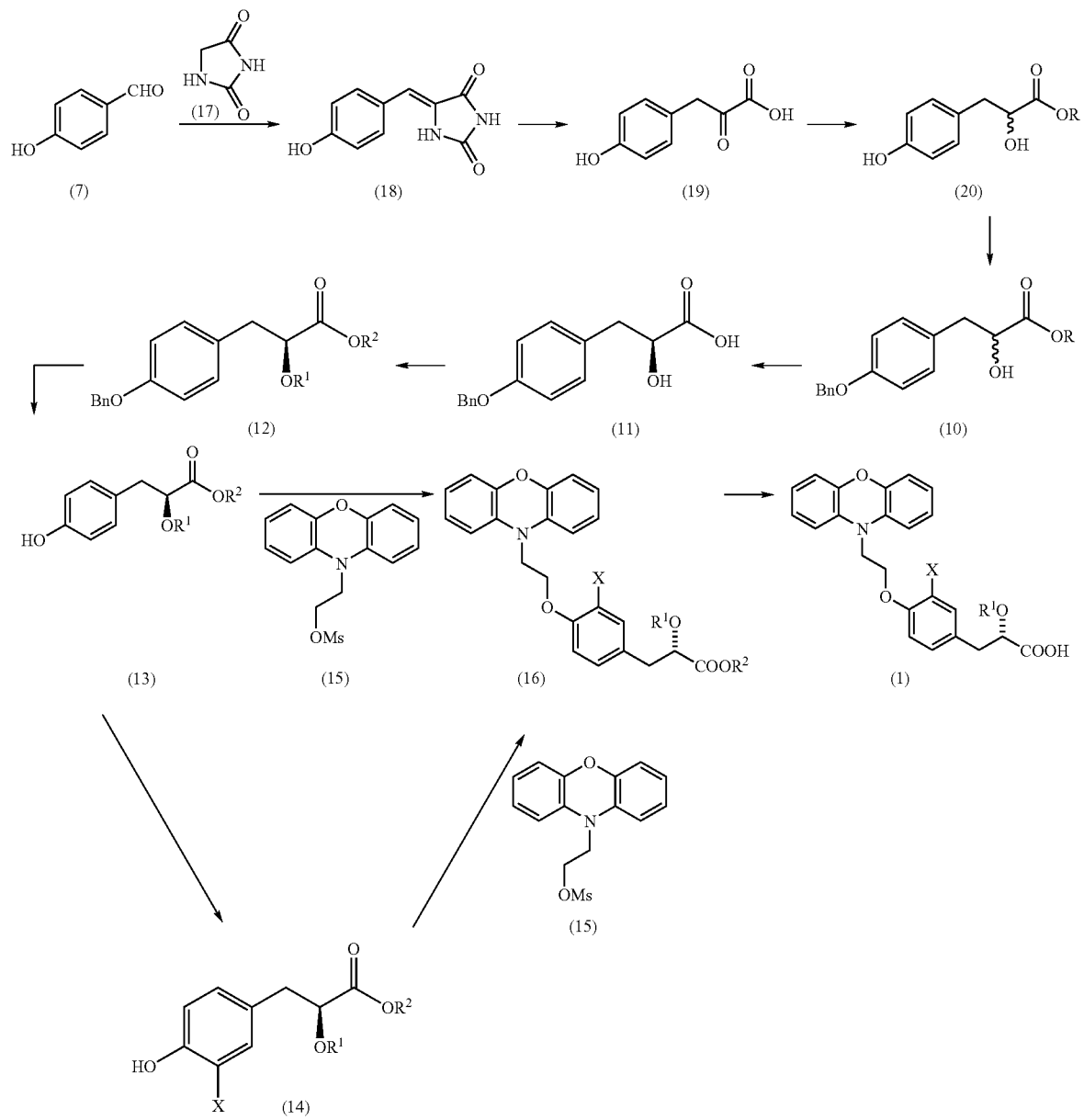

Reaction of p-hydroxybeuzaldehyde of the formula (7) with hydantoin of the formula (17) affords the unsaturated compound of the formula (18), which on hydrolysis gives the pyruvic acid derivative of the formula (19). The pyruvic acid derivative of the formula (19) is reduced in solvents such as methanol, ethanol, propanol, ethylacetate, and the like in the presence of Raney. Ni, $H_2$/Pd—C to give the racemic hydroxy ester of the formula (20) (R represents hydrogen or lower alkyl group such as $C_1$–$C_6$ alkyl preferably methyl, ethyl and the like). The compound of formula (20) (where R represents hydrogen) has to be esterified using alcohol/sulphuric acid mixture to produce compound of formula (20) (where R represents lower alkyl group such as $C_1$–$C_6$ alkyl, preferably methyl, ethyl and the like). The alcohol used for esterification may be selected from methanol, ethanol and the like. The compound of formula (20) (where R represents lower alkyl group such as $C_1$–$C_6$ alkyl, preferably methyl, ethyl and the like) on selective benzylation of the phenolic group provides the compound of the formula (10). Hydrolysis of the compound of the formula (10) followed by its resolution using chiral amines such as R(+)-α-methylbenzyl-amine, cinchonidine, ephednine. S(+) phenylglycinol, n-octylglucosamine and the like lives the optically active hydroxy acid of the formula (11). Alkylation of the compound having the formula (11) using alkylating agents such as diethylsulphate, ethyliodide, methyliodide, dimethylsulhate and the like, in the presence of a base such as NaH, NaOH, KOH, t-BuOK, $K_2CO_3$, $NaHCO_3$ and the like, affords the compound of the formula (12) where $R^1$ represents hydrogen or lower alkyl group such as $C_1$–$C_6$ alkyl preferably methyl, ethyl, propyl and the like, $R^2$ represents lower alkyl group such as $C_1$–$C_6$ alkyl, preferably methyl, ethyl, propyl and the like. The compound of the formula (12) upon debenzylation using reagents such as $H_2$/Pd—C, HCl/AcOH, and the like, in the presence of solvents such as THF, n-hexanol, n-octanol, 1,4-dioxane, AcOH and the like, gives the substituted phenol of the formula (13) defined earlier. The compound of the formula (13) is converted to a compound of formula (14) defined earlier using suitable halogenating agents such as ICl/HCl, $I_2$/KI, $Cl_2$/$H^+$, $Br_2$/AcOH and the like. The optically active compound of the formula (13) or the compound of formula (14) reacts with the phenoxazinyl mesylate of the formula (15) to give the ester of the formula (16) which on hydrolysis employing conventional methods yields the required compound of the formula (1) in an optically pure form. However, in the event of a small amount of racemization, if any, during the course of converting the intermediate of the formula (11) to the final compound of the formula (1), resolution can easily be done employing chiral amines without loosing much of the compound of the formula (1).

The present invention also provides still another improved process for the preparation of compound of the formula (1) described above which comprises (i) reacting p-hydroxybenzaldehyde of the formula (7) with hydantoin of the formula (17) by conventional methods to yield a compound of the formula (18), (ii) hydrolysing the compound of the formula (18) by conventional methods to yield a compound of the formula (19), (iii) reducing the compound of the formula (19) by conventional methods to yield a compound of the formula (20), where R represents hydrogen or lower alkyl group, (iv) benzylating the compound of the formula (20) by conventional methods to yield a compound of the formula (10) where R is as defined earlier, (v) alkylating the compound of the formula (10) using alkylating agent in the presence of a base to obtain a compound of the formula (12a) where $R^1$ represents hydrogen or lower alkyl group. $R^2$ represents lower alkyl group, (vii) debenzylating the compound of the formula (12a) by conventional methods to produce the compound of formula (13a) where $R^1$ and $R^2$ are as defined above, if desired, (viii) converting the compound of formula (13a) to a compound of formula (14a) where X represents halogen atom, $R^1$ and $R^2$ are as defined above by conventional methods, (viii) reacting either the compound of formula (13a) or the compound of formula (14a) with phenoxazinyl mesylate of the formula (15) to give the ester of the formula (4) where X represents hydrogen or halogen atom, $R^1$ and $R^2$ are as defined above, (ix) hydrolysing the compound of the formula (4) by conventional methods to yield the racemic compound of the formula (5) where X represents hydrogen or halogen atom, $R^1$ and $R^2$ are as defined above, and (x) chemically resolving the compound of formula (5) by employing chiral amines to the final compound of formula (1) optionally through an intermediate amide of the formula (6) where X represents hydrogen or halogen atom, and $R^1$ and $R^2$ are as defined above.

The process explained above is as shown in scheme-5 below:

Scheme-5

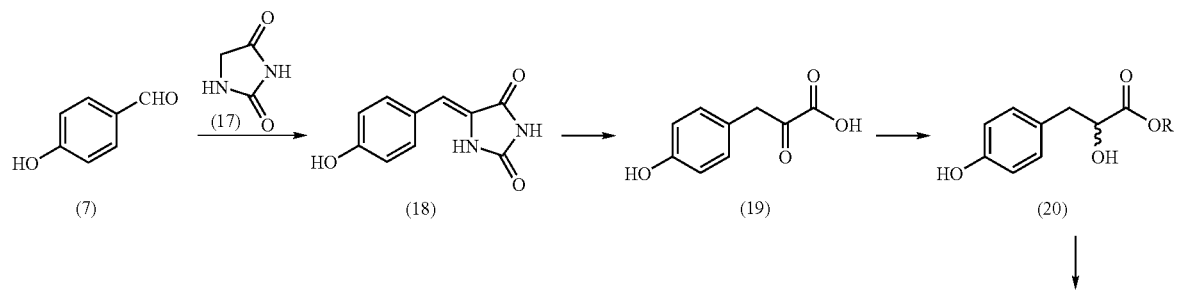

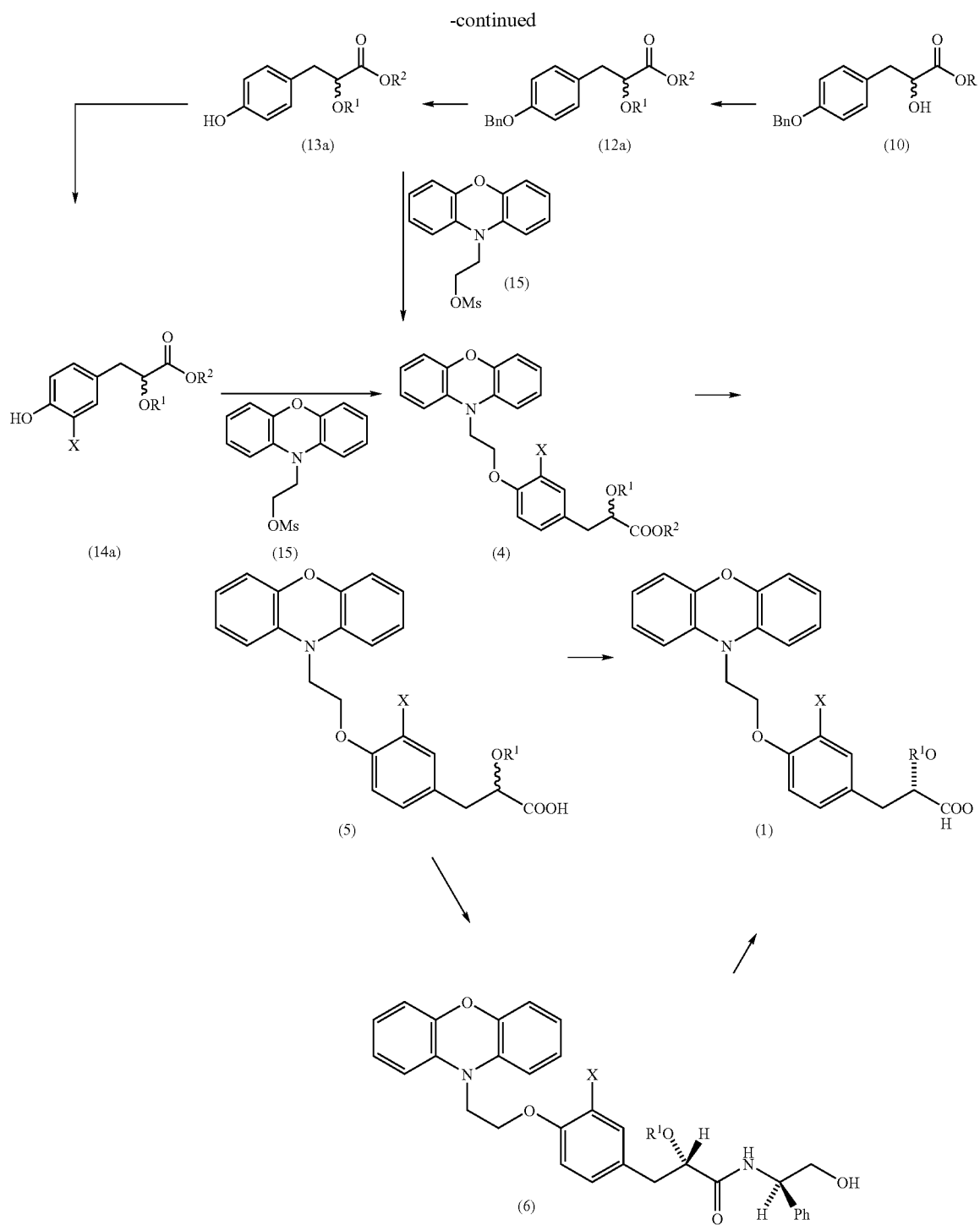

Reaction of p-hydroxybenzaldehyde of the formula (7) with hydantoin of the formula (17) affords the unsaturated compound of the formula (18), which on hydrolysis gives the pyruvic acid derivative of the formula (19). The pyruvic acid derivative of the formula (19) is reduced in solvents such as methanol, ethanol, propanol, ethylacetate, and the like, in the presence of Raney Ni, $H_2$/Pd—C to give the racemic hydroxy ester of the formula (20) (R represents hydrogen or lower alkyl group such as $C_1$–$C_6$ alky, preferably methyl, ethyl and the like). The compound of formula (20) (where R represents hydrogen) has be esterified using alcohol/sulphuric acid mixture to produce compound of formula (20) (where R represents lower alkyl group such as. $C_1$–$C_6$ group; preferably methyl, ethyl and the like). The alcohol used for esterification may be selected from methanol, ethanol and the like. The compound of formula (20) (where R represents lower alkyl group such as $C_1$–$C_6$ group, preferably-methyl, ethyl and the like) on selective benzylation of the phenolic group provides the compound of the formula (10), which on alkylation using alkylating agents such as diethylsuphate, ethyliodide, methyliodide, dimethylsulphate and the like, in the presence of a base such as NaH, NaOH, KOH, t-BuOK, $K_2CO_3$, $NaHCO_3$, and the like, affords the compound of the formula (12a) where $R^1$ represents hydrogen or lower alkyl group such as ($C_1$–$C_6$), alkyl, preferably methyl, ethyl, propyl and the like, $R^2$ represents lower alkyl group such as ($C_1$–$C_6$) alkyl, preferably methyl, ethyl, propyl and the like. The compound of the formula (12a) upon debenzylation using reagents such as $H_2$/Pd—C, HCl/AcOH, and the like in the presence of solvents such as THF, n-octanol, n-hexanol, 1,4-dioxane, AcOH and the like, gives the substituted phenol of the formula (13a). The compound of the formula (13a) is converted to a compound of formula (14a) using suitable halogenating agents such as ICl/HCl, $I_2$/KI, $Cl_2$/$H^+$, $Br_2$/AcOH and the like. The compound of the formula (13a) or the compound of formula (14a) reacts with the phenoxazinyl mesylate having the formula (15) to give the ester of the formula (4) which on hydrolysis employing conventional methods and resolution using chiral amines such as R(+)-α-methylbenzylamine, S(+)-phenyl-glycinol, cinchonidine, ephedrine, n-octylglucosamine and the like yields the required compound of the formula (1) in an optically pure form.

The present invention further provides yet another improved process for the preparation of compounds of the formula (1) described above which comprises:

(i) selectively benzylating L-tyrosine of the formula (21) by conventional methods to yield a compound of the formula (22), (ii) diazotizing the compound of the formula (22) in the presence of an acidic reagent and an organic solvent to produce compound of the formula (11') (where R' represents hydrogen or acetyl group), (iii) if desired, hydrolysing the compound of formula (11') (where R' represents acetyl group) to a compound of formula (11') (where R' represents hydrogen) by conventional methods, (iv) converting the compound of the formula (11') (where R' represents hydrogen) to the alkyl compound of the formula (12) where $R^1$ represents hydrogen or lower alkyl group, $R^2$ represents lower alkyl group in one pot, by treating it with an alkylating agent in the presence of strong base, (v) debenzylating the compound of the formula (12) by conventional methods to produce the compound of the formula (13) where $R^1$ and $R^2$ are as defined above, if desired, (vi) converting the compound of formula (13) to a compound of formula (14) where X represents halogen, and $R^1$ and $R^2$ are as defined above, by conventional methods, (vii) reacting either the compound of the formula (13) or the compound of formula (14) with phenoxazinyl mesylate of the formula (15) to give the ester of the formula (16) where X represents hydrogen or halogen atom, and $R^1$ and $R^2$ are as defined above, (viii) hydrolysing the compound of the formula (16) by conventional methods to yield the compound of the formula (1) defined above, and if desired, (ix) unresolved compound of formula (1) if any may be chemically resolved by employing chiral amines.

The process is shown in scheme-6 below:

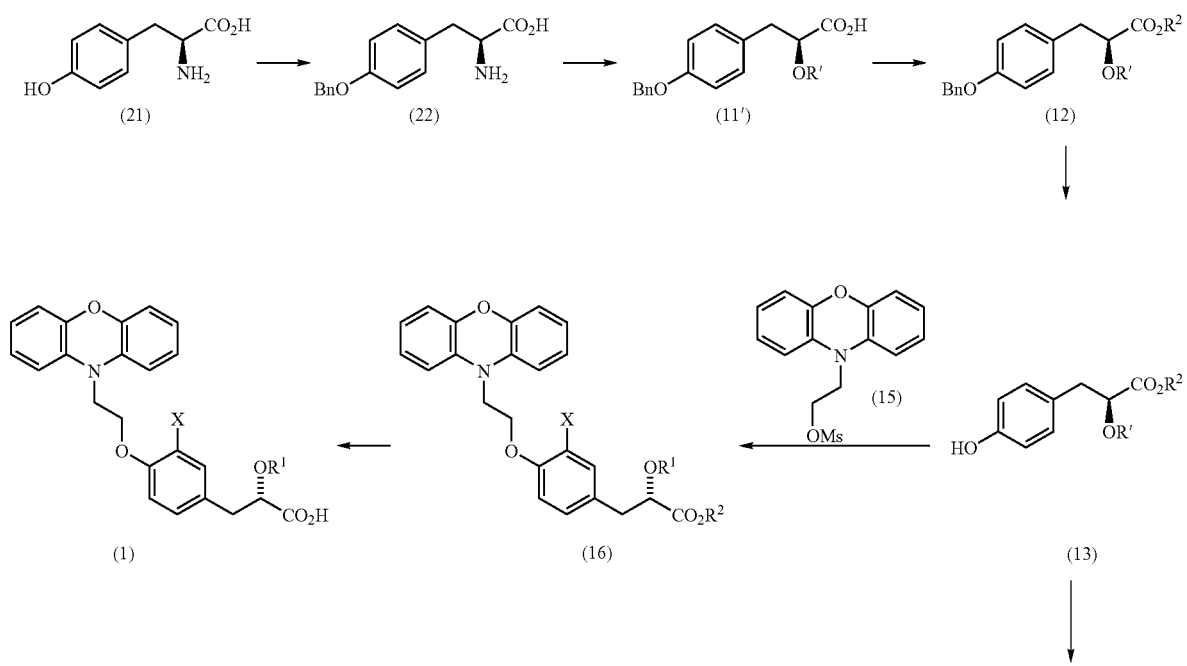

Scheme-6

-continued

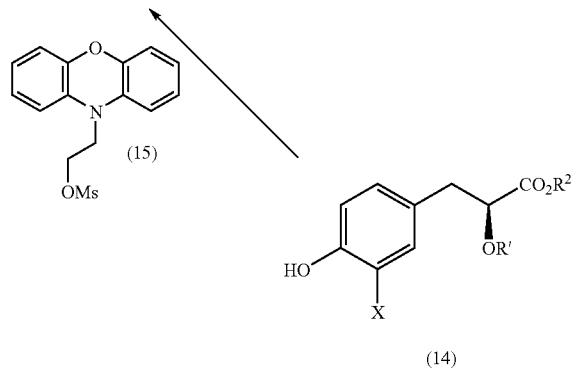

The process of the present invention starts from L-tyrosine of the formula (21) by selectively benzylating it to afford the compound of the formula (22). Diazotisation of the compound of the formula (22) under acidic conditions using acids such as sulfuric acid, HCl, acetic acid and the like in appropriate organic solvent such as CHCl$_3$, 1,4-dioxane, THF, acetone, and the like gives the compound of the formula (11') (where R' represents hydrogen or acetyl group) in more than 98% ee (enantiomeric excess). Hydrolysis of the compound of formula (11') (where R' represents acetyl group) to a compound of formula (11') (where R' represents hydrogen) may be carried out using conventional hydrolysing agents such as NaOH, KOH, LiOH, Ba(OH)$_2$, and the like. Conversion of the compound of the formula (11') (where R' represents hydrogen) to the alkylated compound of the formula (12) where $R^1$ represents hydrogen or lower alkyl group such as ($C_1$–$C_6$) alkyl preferably methyl, ethyl, propyl and the like, $R^2$ represents lower alkyl group such as ($C_1$–$C_6$) alkyl preferably methyl, ethyl, propyl and the like, in one pot is achieved using alkylating agents such as diethylsulphate, ethyliodide, methyliodide, dimethyl-sulphate and the like in the presence of a strong base such as NaH, NaOH, KOH, t-BuOK, $K_2CO_3$, NaHCO$_3$, and the like. Debenzylation of the compound of the formula (12) by conventional methods with H$_2$/Pd—C, HCl/AcOH, and the like, in the presence of solvents such as THF, n-hexanol, n-octanol, 1,4-dioxane, AcOH and the like, afforded the required crucial intermediate compound of the formula (13) in very good yield (95%) and purity (95%). The compound of formula (13) is converted to a compound of formula (14) using suitable halogenating agents such as ICl/HCl, I$_2$/KI, Cl$_2$/H$^+$, Br$_2$/AcOH and the like. The optically active compound of the formula (13) or the compound of formula (14) is reacted with the phenoxazinyl mesylate having the formula (15) to give the ester of the formula (16) which on hydrolysis employing conventional methods yields the required compound of the formula (1) in an optically pure form and yield of 95%. However, in the event of a small amount of racemization, if any, resolution can easily be done employing chiral amines such as R(+)α-methylbenzylamine, S(+)-phenylglycinol, cinchonidine, ephedrine, n-octyl-glucosamine and the like.

The present invention also provides an improved process for the preparation of compound of formula (13) where $R^1$ represents hydrogen or lower, alkyl group and $R^2$ represents lower alkyl group which comprises:

(i) selectively benzylating L-tyrosine of the formula (21) by conventional method to yield a compound of the formula (22), (ii) diazotizing the compound of the formula (22) in the presence of an acidic reagent and an organic solvent to produce compound of the formula (11') (where R' represents hydrogen or acetyl group), if desired, (iii) hydrolysing the compound of formula (11') (where R' represents acetyl group) to a compound of formula (11') (where R' represents hydrogen) by conventional methods, (iv) converting the compound of the formula (11') (where R' represents hydrogen) to the compound of the formula (12) where $R^1$ represents hydrogen or lower alkyl group, $R^2$ represents lower alkyl group in one pot, by treating it with an alkylating agent in the presence of strong base, and (v) debenzylating the compound of the formula (12) by conventional methods to produce the compound of the formula (13) where $R^1$ and $R^2$ are as defined above.

The process is shown in scheme-7 below:

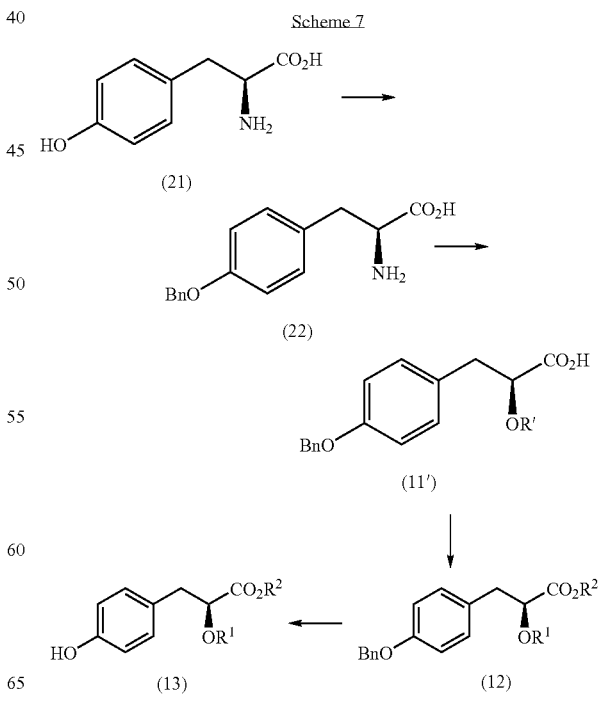

The process of the present invention starts from L-tyrosine of the formula (21) by selectively benzylating it to afford the compound of the formula (22). Diazotization of the compound of the formula (22) under acidic conditions acids using an acid such as sulfuric acid, HCl, acetic acid and the like in appropriate organic solvent such as $CHCl_3$, 1,4-dioxane, THF, acetone, and the like gives the compound of the formula (11') (where R' represents hydrogen or acetyl group) in more than 98% ee (enantiomeric excess). Hydrolysis of the compound of formula (11') (where R' represents acetyl group) to a compound of formula (11') (where R' represents hydrogen) may be carried out using conventional hydrolysing agents such as NaOH, KOH, LiOH, $Ba(OH)_2$, and the like. Conversion of the compound of the formula (11') (where R' represents hydrogen) to the alkylated compound of the formula (12) where R' represents hydrogen or lower alkyl group such as $(C_1-C_6)$ alkyl, preferably methyl, ethyl, propyl and the like, $R^2$ represents lower alkyl group such as $(C_1-C_6)$ alkyl, preferably methyl, ethyl, propyl and the like, in one pot is achieved using alkylating agents such as diethyl sulphate, ethyl iodide, and the like in the presence of a strong base such as NaH, NaOH, KOH, t-BuOK, and the like. Debenzylation of the compound of the formula (12) by conventional methods with $H_2$/Pd—C, HCl/AcOH, and the like, in the presence of solvents such as THF, n-hexanol, n-octanol, 1,4-dioxane, AcOH and the like, afforded the required of the formula (13) in very good yield (95%) and purity (95%).

The present invention is described in detail with examples given below which are provided by way of illustration only and therefore should not be construed to limit the scope of the invention.

EXAMPLE 1

Step-i:

Preparation of 4-benzyloxybenzaldehyde of the Formula (8):

4-Hydroxybenzaldehyde of the formula (7) (100 g), potassium carbonate (226 g) and dimethylformamide (500 ml) were taken in a reaction flask and stirred for 15 minutes. Benzylchloride (114 g) was then added at room temperature and the reaction mass was stirred at the same temperature for a period of 8–10 h. The progress of the reaction was monitored with TLC. After completion of the reaction, the reaction mixture was dumped into ice water and extracted with toluene. The combined organic extracts were washed with 10% aq. sodium hydroxide solution followed by water. The solvent was removed under reduced pressure and the resulting residue was tritarated with pet ether to afford the title compound of the formula (8) (160–165 g, 93–95%).

Step-ii:

Preparation of ethyl-2,3-epoxy-3-(4-benzyloxyphenyl) propionate of the Formula (9):

4-Benzyloxybenzaldehyde of the formula (8) (100 g) obtained according to the procedure described in step (i) above, was added to a solution of sodium ethoxide (64 g) in absolute ethanol followed by the addition of ethylchloroacetate (87 g) over a period of 30–45 minutes, maintaining ambient temperature. The reaction mixture was stirred at the same temperature for 3–5 h. The progress of the reaction was monitored with TLC. After completion of the reaction, the reaction mixture was dumped into ice water and stirred for 5–10 minutes. The solid thus obtained was filtered, washed with water and dried to afford the title compound of the formula (9) (126–129 g, 90–92%).

Step-iii:

Preparation of racemic ethyl 2-hydroxy-3-(4-benzyloxyphenyl)propionate of the Formula (10):

A mixture of ethyl-2,3-epoxy-3-(4-benzyloxyphenyl)propionate of the formula (9) (125 g) obtained according to the procedure described in step (ii) above, 5% Pd/C catalyst (12.5 g) and 1,4-dioxane (750 ml) was hydrogenated at room temperature at 5–10 psi of hydrogen pressure for a period of 10–15 h. The progress of the reaction was monitored by TLC. After completion of the reaction, the catalyst was filtered and the solvent was removed under reduced pressure to afford the title compound of the formula (10) (100–105 g, 80–83%).

Step-iv:

Preparation of S(−)-2-hydroxy-3-(4-benzyloxyphenyl) propionic acid of the Formula (11):

A mixture of racemic ethyl 2-hydroxy-3-(4-benzyloxyphenyl)propionate of the formula (10) (100 g) obtained according to the procedure described in step (iii) above and 10% aq. sodium hydroxide solution (500 ml) was stirred at room temperature for a period of 1–2 h. The progress of the reaction was monitored by TLC. After completion of the reaction, the reaction mixture was acidified with dil. hydrochloric acid at 15–20° C. and the solid thus obtained was filtered and washed with water to afford racemic 2-hydroxy-3(4-benzyloxyphenyl)propionic acid (72–77 g, 80–85%).

To a solution of racemic 2-hydroxy-3-(4-benzyloxyphenyl)propionic acid (75 g) obtained according to the procedure described above in ethylacetate (1.1 L) was added R(+)-α-methylbenzylamine (33 g) and the mixture was stirred at room temperature for a period of 2–4 h. The solid thus obtained was filtered and the acid was regenerated after acidification to afford S(−)-2-hydroxy-3-(4-benzyloxyphenyl)propionic acid of the formula (11), (33–35 g, 44–47%). The R(+)-α-hydroxy acid obtained from the mother liquor was racemised and mixed with subsequent batches for resolution. The overall yield obtained by several such reprocesses was ~90–95%.

Step-v:

Preparation of S(−)-ethyl 2-ethoxy-3-(4-benzyloxyphenyl)propionate of the Formula (12):

To a slurry of sodium hydride (60% suspension in oil, 13 g) and dimethyl formamide (70 ml) was added a solution of S(−)-2-hydroxy-3-(4-benzyloxyphenyl) propionic acid of the formula (11) (35 g) obtained according to the procedure described in step (iv) above, in dimethylformamide (105 ml) at 5–10° C. over a period of 15–30 minutes. The temperature was allowed to attain room temperature and maintained at the same temperature for 1–3 hours. Ethyl iodide (62 g) was added slowly by maintaining the temperature at 25–30° C. over a period of 2–3 hours. The progress of the reaction was monitored by TLC. After completion of the reaction, the reaction mixture was dumped into ice water and extracted with toluene. The combined organic extracts were washed with water and the solvent was removed under reduced pressure to afford S(−)-α-ethoxy ethyl ester of the formula (12) (41–42 g, 98–99%).

Step-vi:

Preparation of S(−)-ethyl 2-ethoxy-3-(4-hydroxyphenyl) propionate of the Formula (13):

A mixture of S(−)-ethyl 2-ethoxy-3-(4-benzyloxyphenyl) propionate of the formula (12) (40 g) obtained according to the procedure described in step (v) above, 5% Pd/C catalyst (8 g) and tetrahydrofuran (120 ml) was subjected to hydrogenation at room temperature and 50–60 psi of hydrogen pressure for a period of 8–12 hours. The progress of the reaction was monitored by TLC. After completion of the reaction, the catalyst was filtered off and the solvent was removed under reduced pressure to afford debenzylated product of the formula (13) (28–29 g, 97–98%).

Step-vii:

Preparation of S(−)-ethyl 3-[4-[2-(phenoxazin-10-yl) ethoxy]phenyl]-2-ethoxypropionate of the Formula (16):

A mixture of S(−)-ethyl 2-ethoxy-3-(4-hydroxyphenyl) propionate of the formula (13) (25 g) obtained according to the procedure described in step (vi) above, the mesylate of the formula (15) (32 g), potassium carbonate (36 g) and toluene (250 ml) was refluxed for a period of 15–20 hours. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title compound of the formula (16) (46–47 g, 98–99%), as an oily material.

Step-viii:

Preparation of S(−)-3-[4-[2-(phenoxazin-10-yl)ethoxy] phenyl]-2-ethoxypropanoic acid of the Formula (1):

To a mixture of S(−)-ethyl 3-[4-[2-(phenoxazin-10-yl) ethoxy]phenyl]-2-ethoxypropionate of the formula (16) (45 g) obtained according to the procedure described in step (vii) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (16), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded the title compound of the formula (1) (38–39 g, 90–92%).

EXAMPLE 2

Step-i:

Preparation of 4-benzyloxybenzaldehyde of the Formula (8):

4-Hydroxybenzaldehyde of the formula (7) (100 g), potassium carbonate (226 g) and dimethylformamide (500 ml) were taken in a reaction flask and stirred for 15 minutes. Benzylchloride (114 g) was then added at room temperature and the reaction mass was stirred at the same temperature for a period of 8–10 h. The progress of the reaction was monitored by TLC. After completion of the reaction, the reaction mixture was dumped into ice water and extracted with toluene. The combined organic extracts were washed with 10% aq. sodium hydroxide solution followed by water. The solvent was removed under reduced pressure and the resulting residue was triturated with pet. ether to afford the title compound of the formula (8) (160–165 g, 93–95%).

Step-ii:

Preparation of ethyl-2,3-epoxy-3-(4-benzyloxyphenyl) propionate of the Formula (9):

4-Benzyloxybenzaldehyde of the formula (8) (100 g) obtained according to the procedure described in step (i) above was added to a solution of sodium ethoxide (64 g) in absolute ethanol followed by the addition of ethylchloroacetate (87 g) over a period of 30–45 minutes, maintaining ambient temperature. The reaction mixture was stirred at the same temperature for 3–5 h. The progress of the reaction was monitored by TLC. After completion of the reaction, the reaction mixture was dumped into ice water and stirred for 5–10 minutes. The solid thus obtained was filtered, washed with water and dried to afford the title compound of the formula (9) (126–129 g, 90–92%).

Step-iii:

Preparation of Racemic Ethyl 2-hydroxy-3-(4-benzyloxyphenyl)propionate of the Formula (10):

A mixture of ethyl-2,3-epoxy-3-(4-benzyloxyphenyl)propionate of the formula (9) (125 g) obtained according to the procedure described in step (ii) above, 5% Pd/C catalyst (12.5 g) and 1,4-dioxane (750 ml) was hydrogenated at room temperature at 5–10 psi of hydrogen pressure for a period of 10–15 h. The progress of the reaction was monitored by TLC. After completion of the reaction, the catalyst was filtered and the solvent was removed under reduced pressure to afford the title compound of the formula (10) (100–105 g, 80–83%).

Step-iv:

Preparation of Racemic Ethyl 2-ethoxy-3-(4-benzyloxyphenyl)propionate of the Formula (12a):

To a slurry of sodium hydride (60% suspension in oil, 7.5 g) and dimethyl formamide (70 ml) was added a solution of the racemic ethyl 2-hydroxy-3(4-benzyloxyphenyl)propionate of the formula (10) (40 g) obtained according to the procedure described in step (iii) above in dimethylformamide (105 ml) at 5–10° C. over a period of 15–30 minutes. The temperature was allowed to attain room temperature and maintained at the same temperature for 1–3 h. Ethyl iodide (36 g) was added slowly by maintaining the temperature at 5–30° C. over a period of 2–3 hours. The progress of the reaction was monitored by TLC. After completion of the reaction, the reaction mixture was dumped into ice water and extracted with toluene. The combined organic extracts were washed with water and the solvent was removed under reduced pressure to afford title compound of the formula (12a) (47–48 g, 98–99%).

Step-v:

Preparation of Racemic Ethyl 2-ethoxy-3-(4-hydroxyphenyl)propionate of the Formula (13a):

A mixture of racemic ethyl 2-ethoxy-3-(4-benzyloxyphenyl)propionate of the formula (12a) (40 g) obtained according to the procedure described in step (iv) above, 5% Pd/C catalyst (8 g) and tetrahydrofuran (120 ml) was subjected to hydrogenation at room temperature and 50–60 psi of hydrogen pressure for a period of 8–12 h. The progress of the reaction was monitored by TLC. After completion of the reaction, the catalyst was filtered off and the solvent was removed under reduced pressure to afford the title compound of the formula (13a) (28–29 g, 97–98%).

Step-vi:

Preparation of racemic ethyl 3-[4-[2-(phenoxazin-10-yl) ethoxy]phenyl]-2-ethoxypropionate of the Formula (4):

A mixture of racemic ethyl 2-ethoxy-3-(4hydroxyphenyl) propionate of the formula (13a) (25 g) obtained according to the procedure described in step (v) above, the mesylate of the formula (15) (32 g), potassium carbonate (36 g) and toluene (250 ml) was refluxed for a period of 15–20 h. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title of the formula (4) (46–47 g, 98–99%) as an oily material.

Step vii:

Preparation of Racemic 3-[4-[2-(phenoxazin-10-yl) ethoxyl]phenyl]-2-ethoxypropanoic acid of the Formula (5):

To a mixture of racemic ethyl 3-[4-[2-(phenoxazin-10-yl) ethoxy]phenyl]-2-ethoxypropionate of the formula (4) (45 g) obtained according to the procedure described in step (vi) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (4), the reaction mass was diluted with 225 ml of water and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded racemic acid of the formula (5) as an off-white to white solid which was filtered and dried at room temperature (~30° C.), (38–39 g, 90–92%).

Step-viii:

Preparation of S(−)-3-[4-[2-(phenoxazin-10-yl)ethoxy] phenyl]-2-ethoxypropanoic acid of the Formula (1):

To a solution of racemic 3-[4-[2-(phenoxazin-10-yl) ethoxy]phenyl]-2-ethoxypropanoic acid of the formula (5) (35 g) obtained according to the procedure described in step (vii) above in ethylacetate (525 ml) was added R(+)-α-methylbenzyl-amine (10 g) and the mixture was stirred at room temperature for a period of 2–4 h. The solid thus obtained was filtered and the acid was regenerated after acidification to afford (15–17 g, 44–47%) S(−)-α-ethoxy acid of the formula (1). The R(+)-α-ethoxy acid obtained from the mother liquor was racemised and mixed with subsequent batches for resolution The overall yield obtained by several such reprocesses was ~90–95%.

EXAMPLE 3

Step-i:

Preparation of 4-benzyloxybenzaldehyde of the Formula (8):

4-Hydroxybenzaldehyde of the formula (7) (100 g), potassium carbonate (226 g) and acetone (500 ml) were taken in a reaction flask and stirred for 15 minutes. Benzylbromide (154 g) was then added at room temperature and the reaction mass was stirred at the same temperature for a period of 8–10, h. The progress of the reaction was monitored by TLC. After completion of the reaction, the reaction mixture was dumped into ice water and extracted with toluene. The combined organic extracts were washed with 10% aq. sodium hydroxide solution followed by water. The solvent was removed under reduced pressure and the resulting residue Visas triturated with pet. ether to afford 4-benzyloxybenzaldehyde of the formula (8) (160–165 g, 93–95%).

Step-ii:

Preparation of ethyl-2,3-epoxy-3-(4-benzyloxyphenyl) propionate of the Formula (9):

4-Benzyloxybenzaldehyde of the formula (8) (100 g) obtained according to the procedure described in step (i) above was added to a solution of sodium methoxide (64 g) in dry methanol followed by the addition of methylchloroacetate (87 g) over a period of 30–45 minutes, maintaining ambient temperature. The reaction mixture was stirred at the same temperature for 3–5 h. The progress of the reaction was monitored by TLC. After completion of the reaction, the reaction mixture was dumped into ice water and stirred for 5–10 minutes. The solid thus obtained was filtered, washed with water and dried to afford the title compound of the formula (9) (126–129 g, 90–92%).

Step-iii:

Preparation of racemic ethyl 2-hydroxy-3-(4-benzyloxyphenyl)propionate of the Formula (10):

A mixture of ethyl-2,3-epoxy-3-(4-benzyloxyphenyl)propionate of the formula (9) (125 g) obtained according to the procedure described in step (ii) above, Raney Nickel catalyst (12.5 g) and 1,4-dioxane (750 ml) was hydrogenated at room temperature at 30–40 psi of hydrogen pressure for a period of 8–10 hours. The progress of the reaction was monitored by TLC. After completion of the reaction, the catalyst was filtered and the solvent was removed under reduced pressure to afford the title compound of the formula (10) (100–105 g, 80–83%).

Step-iv:

Preparation of S(−)-2-hydroxy-3-(4-benzyloxyphenyl) propionic Acid of the Formula (11):

A mixture of racemic ethyl 2-hydroxy-3-(4-benzyloxyphenyl)propionate of the formula (10) (100 g) obtained according to the procedure described in step (iii) above and 10% aq. sodium hydroxide solution (500 ml) was stirred at room temperature for a period of 1–2 h. The progress of the reaction was monitored by TLC. After completion of the reaction, the reaction mixture was acidified with dil. hydrochloric acid at 15–20° C. and the solid thus obtained was filtered and washed with water to afford racemic 2-hydroxy acid (72–77 g, 80–85%).

To a solution of racemic 2-hydroxy-3-(4-benzyloxyphenyl)propionic acid (75 g) obtained according to the procedure described above in ethylacetate (1.1 L) was added S(+)phenylglycinol (38 g) and the mixture was stirred at room temperature for a period of 2–4 hours. The solid thus obtained was filtered and the acid was regenerated after acidification to afford S(−)-α-hydroxy acid of the formula (11) (33–35 g, 44–47). The R(+)-α-hydroxy acid obtained from the mother liquor was racemised and mixed with subsequent batches for resolution. The overall yield obtained by several such reprocesses was ~90–95%.

Step-v:

Preparation of S(−)-ethyl 2-ethoxy-3-(4-benzyloxyphenyl)propionate of the Formula (12):

To a mixture of S(−)-2-hydroxy-3-(4-benzyloxyphenyl) propionic acid of the formula (11) (35 g) obtained according to the procedure described in step (iv) above, potassium hydroxide (18 g), 1,4-dioxane (350 ml) and water (175 ml) was added diethylsulphate (38 g) at 60° C. over a period of 1–2 h. The reaction was stirred at the same temperature for a period of 15–20 h. The progress of the reaction was monitored by TLC. After completion of the reaction, the reaction mixture was dumped into ice water and extracted with toluene. The combined organic extracts were washed with water and the solvent was removed under reduced pressure to afford the title compound of the formula (12) (34–35 g, 80–82%).

Step-vi:

Preparation of S(−)-ethyl 2-ethoxy-3-(4-hydroxyphenyl) propionate of the Formula (13):

A mixture of S(−)-ethyl 2-ethoxy-3-(4-benzyloxyphenyl) propionate of the formula (12) (40 g) obtained according to the procedure described in step (v) above, 5% Pd/C (8 g) and 1,4-dioxane (200 ml) was subjected to hydrogenation at room temperature and 50–60 psi of hydrogen pressure for a period of 12–15 h. The progress of the reaction was monitored by TLC. After completion of the reaction, the catalyst was filtered off and the solvent was removed under reduced pressure to afford debenzylated compound of the formula (13) (28–29 g, 97–98%).

Step-vii:

Preparation of S(−)-ethyl 3-[4-[2-(phenoxazin-10-yl) ethoxy]phenyl]-2-ethoxypropionate of the Formula (16):

A mixture of S(−)-ethyl 2-ethoxy-3-(4-hydroxyphenyl) propionate of the formula (13) (25 g) obtained according to the procedure described in step (vi) above, the mesylate of the formula (15) (32 g), potassium carbonate (36 g) and dimethyl formamide (125 ml) was refluxed for a period of 3–6 hours. The progress of the reaction was monitored by TLC. After completion of the reaction, the reaction mass was dumped into ice water and extracted with toluene. The combined organic extracts were washed with water and concentrated under vacuum to afford the title compound of the formula (16) (46–47 g, 98–99%), as an oily material.

Step-viii:

Preparation of S(−)-3-[4-[2-(phenoxazin-10-yl)ethoxy] phenyl]-2-ethoxypropanoic acid of the Formula (1):

To a mixture of S(−)-ethyl 3-[4-[2-(phenoxazin-10-yl) ethoxy]phenyl]-2-ethoxy-propionate of the formula (16) (45 g) obtained according to the procedure described in step (vii) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of formula (16), the reaction mass was diluted with water (225 ml) and washed with toluene to remove the impurities. The aqueous layer was acidified with dilute hydrochloric acid and extracted with toluene. The combined organic extracts were washed with water and concentrated under reduced pressure to half the volume and treated with activated charcoal. Filtration of the charcoal followed by concentration of toluene to ~50 ml and precipitation with pet. ether (~30° C.) afforded the compound of the formula (1) (38–39 g, 90–92%).

Example 4

Step-i:

Preparation of 4-benzyloxybenzaldehyde of the Formula (8):

4-Hydroxybenzaldehyde of the formula (7) (100 g), potassium carbonate (226 g) and acetone (500 ml) were taken in a reaction flask and stirred for 15 minutes. Benzylbromide (154 g) was then added at room temperature and the reaction mass was stirred at the same temperature for a period of 8–10 h. The progress of the reaction was monitored by TLC. After completion of the reaction, the reaction mixture was dumped into ice water and extracted with toluene. The combined organic extracts were washed with 10% aq. sodium hydroxide solution followed by water. The solvent was removed under reduced pressure and the resulting residue was triturated with pet. ether to afford 4-benzyloxybenzaldehyde of the formula (8) (160–165 g, 93–95%).

Step-ii:

Preparation of ethyl-2,3 epoxy-3-(4-benzyloxyphenyl) propionate of the Formula (9):

4-Benzyloxybenzaldehyde of the formula (8) (100 g) obtained according to the procedure described in step (i) above was added to a solution of sodium methoxide (64 g) in dry methanol followed by the addition of methylchloroacetate (87 g) over a period of 30–45 minutes, maintaining ambient temperature. The reaction mixture was stirred at the same temperature for 3–5 h The progress of the reaction was monitored by TLC. After completion of the reaction, the reaction mixture was dumped into ice water and stirred for 5–10 minutes. The solid thus obtained was filtered, washed with water and dried to afford the title compound of the formula (9) (126–129 g, 90–92%).

Step-iii:

Preparation of racemic ethyl 2-hydroxy-3-(4-benzyloxyphenyl)propionate of Formula (10):

A mixture of ethyl-2,3-epoxy-3-(4-benzyloxyphenyl)propionate of the formula (9) (125 g) obtained according to the procedure described in step (ii) above. Railey Nickel (12.5 g) and 1,4-dioxane (750 ml) was hydrogenated at room temperature at 30–40 psi of hydrogen pressure for a period of 8–10 hours. The progress of the reaction was monitored by TLC. After completion of the reaction, the catalyst was filtered and the solvent was removed under reduced pressure to afford the title compound of the formula (10) (100–105 g. 80–83%).

Step-iv:

Preparation of racemic ethyl 2-ethoxy-3-(4-benzyloxyphenyl)propionate of the Formula (12a):

A mixture of racemic ethyl 2-hydroxy-3-(4-benzyloxyphenyl)propionate of the formula (10) (70 g) obtained according to the procedure described in step (iii) above. potassium hydroxide (26 g), dimethylsulphoxide (280 ml) and molecular sieves (36 g) was stirred at room temperature for 15 minutes. Ethyliodide (110 g) was added slowly at room temperature over 15 minutes. The reaction was stirred at the same temperature for a period of 15–20 h. The progress of the reaction was monitored by TLC. After completion of the reaction, the reaction mixture was dumped into ice water and extracted with toluene. The combined organic extracts were washed with water and the solvent was removed under reduced pressure to afford title compound of the formula (12a) (61–63 g, 80–82%).

Step-v:

Preparation of racemic ethyl 2-ethoxy-3-(4-hydroxyphenyl)propionate of the Formula (13a):

A mixture of racemic ethyl 2oxy-3-(4-benzyloxyphenyl) propionate of the formula (12a) (40 g) obtained according to the procedure described in step (iv) above, 5% Pd/C catalyst (8 g) and 1,4-thioxane (200 ml) was subjected to hydrogenation at room temperature and 50–60 psi of hydrogen pressure for a period of 8–12 h. The progress of the reaction was monitored by TLC. After completion of the reaction, the catalyst was filtered off and the solvent was removed under reduced pressure to afford the title compound of the formula (13a) (28–29 g, 97–98%)., Step-vi:

Preparation of racemic ethyl 3-[4-[2-(phenoxazin-10-yl) ethoxy]phenyl]-2-ethoxypropionate of the Formula (4):

A mixture of racemic ethyl 2-ethoxy-3-(4-hydroxyphenyl)propionate of the formula (13a) (25 g) obtained according to the procedure described in step (v) above, the mesylate of the formula (15) (32 g), potassium carbonate (36 g) and dimethylsulphoxide (125 ml) was heated at 80–100° C. for a period of 6–8 h. The progress of the reaction was monitored by TLC. After completion of the reaction, the reaction mass was dumped into ice water and extracted with toluene. The combined organic extracts were washed with water and concentrated under vacuum to afford the title compound of the formula (4) (46–47 g, 98–99%) as an oily material.

Step-vii:
Preparation of racemic 3-[4-[2-(phenoxazin-10-yl)ethoxy]phenyl]-2-ethoxypropanoic acid of the Formula (5):

To a mixture of racemic ethyl 3-[4-[2-(phenoxazin-10-yl)ethoxy]phenyl]-2-ethoxypropionate of the formula (4) (45 g) obtained according to the procedure described in step (vi) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (4), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet ether afforded racemic acid of the formula (5) as an off-white to white solid which was filtered and dried at room temperature (~30° C.), (38–39 g, 90–92%).

Step-viii:
Preparation of S(−)-3-[4-[2-(phenoxazin-10-yl)ethoxy]phenyl]-2-ethoxypropanoic acid of the Formula (1):

To a solution of racemic 3-[4-[2-(phenoxazin-10-yl)ethoxy]phenyl]-2-ethoxypropanoic acid of the formula (5) (35 g) obtained according to the procedure described in step (vii) above in acetone (350 ml) was added S(+)phenylglycinol (11.5 g) and the mixture was stirred at room temperature for a period of 2–4 hours. The solid thus obtained was filtered and the acid was regenerated after acidification to afford S(−)-α-ethoxy acid of the formula (1) (15–17 g, 44–47%). The R(+)-α-ethoxy acid obtained from the mother liquor was racemised and mixed with subsequent batches for resolution. The overall yield obtained by several such reprocesses was ~90–95%.

EXAMPLE 5

Step-i:
Preparation of 4-benzyloxybenzaldehyde of the Formula (8):

4-Hydroxybenzaldehyde of the formula (7) (100 g), potassium carbonate (226 g) and dimethylformamide (500 ml) were taken in a reaction flask and stirred for 15 minutes. Benzylchloride (114 g) was then added at room temperature and the reaction mass was stirred at the same temperature for a period of 8–10 h. The progress of the reaction was monitored with TLC. After completion of the reaction, the reaction mixture was dumped into ice water and extracted with toluene. The combined organic extracts were washed with 10% aq. sodium hydroxide solution followed by water. The solvent was removed under reduced pressure and the resulting residue was triturated with pet. ether to afford the title compound of the formula (8) (160–165 g, 93–95%).

Step-ii:
Preparation of ethyl-2,3-epoxy-3(4-benzyloxyphenyl)propionate of the Formula (9):

A mixture of 4-benzyloxybenzaldehyde of the formula (8) (100 g) obtained according to the procedure described in step (i) above, potassium carbonate (260 g), dimethylformamide (500 ml) ethylchloroacetate (86 g) and tetrabutylammonium bromide (1 g) was stirred at room temperature for a period of 30–45 h. The progress of the reaction was monitored with TLC. After completion of the reaction, the reaction mixture was dumped into ice water and stirred for 5–10 minutes. The solid thus obtained was filtered, washed with water and dried to afford the title compound of the formula (9) (126–129 g, 90–92%).

Step-iii:
Preparation of Racemic Ethyl 2-hydroxy-3-(4-benzyloxyphenyl)propionate of the Formula (10):

A mixture of ethyl-2,3-epoxy-3-(4-benzyloxyphenyl)propionate of the formula (9) (125 g) obtained according to the procedure described in step (ii) above, 5% Pd/C catalyst (12.5 g) and 1,4-dioxane (750 ml) was hydrogenated at room temperature at 5–10 psi of hydrogen pressure for a period of 10–15 h. The progress of the reaction was monitored by TLC. After completion of the reaction, the catalyst was filtered and the solvent was removed under reduced pressure to afford the title compound of the formula (10) (100–105 g, 80–83%).

Step-iv:
Preparation of S(−)-2-hydroxy-3-(4-benzyloxyphenyl)propionic acid of the Formula (11):

A mixture of racemic ethyl 2-hydroxy-3-(4benzyloxyphenyl)propionate of the formula (10) (100 g) obtained according to the procedure described in step (iii) above and 10% aq. sodium hydroxide solution (500 ml) was stirred at room temperature for a period of 1–2 h. The progress of the reaction was monitored by TLC. After completion of the reaction, the reaction mixture was acidified with dil. hydrochloric acid at 15–20° C. and the solid thus obtained was filtered and washed with water to afford racemic 2-hydroxy-3-(4-benzyloxyphenyl)propionic acid (72–77 g, 80–85%).

To a solution of racemic 2-hydroxy-3-(4-benzyloxyphenyl)propionic acid (75 g) obtained according to the procedure described above in ethylacetate (1.1 L) was added n-octylglucosamine (81 g) and the mixture was stirred at room temperature for a period of 2–4 hours. The solid thus obtained was filtered and the acid was regenerated after acidification to afford S(−)-α-hydroxy acid of the formula (11) (33–35 g, 44–47. The R(+)-α-hydroxy acid obtained from the mother liquor was racemized and mixed with subsequent batches for resolution. The overall yield obtained by several such reprocesses was ~90–95%.

Step-v:
Preparation of S(−)-ethyl 2-ethoxy-3-(4-benzyloxyphenyl)propionate of the Formula (12):

To a slurry of sodium hydride (60% suspension in oil, 13 g) and dimethyl formamide (70 ml) was added a solution of S(−)-2-hydroxy-3-(4-benzyloxyphenyl) propionic acid of the formula (11) (35 g) obtained according to the procedure described in step (iv) above in dimethylformamide (105 ml) at 5–10° C. over a period of 15–30 minutes. The temperature was allowed to attain room temperature and maintained at the same temperature for 1–3 hours. Ethyl iodide (62 g) was added slowly by maintaining the temperature at 25–30° C. over a period of 2–3 hours. The progress of the reaction was monitored by TLC. After completion of the reaction, the reaction mixture was dumped into ice water and extracted with toluene. The combined organic extracts were washed with water and the solvent was removed under reduced pressure to afford the title compound of the formula (12) (41–42 g, 98–99%).

Step-vi:
Preparation of S(−)-ethyl 2-ethoxy-3-(4-hydroxyphenyl)propionate of the Formula (13):

A mixture of S(−)-ethyl 2-ethoxy-3-(4-benzyloxyphenyl)propionate of the formula (12) (40 g) obtained according to the procedure described in step (v) above, 5% Pd/C catalyst (8 g) and tetrahydrofuran (120 ml) was subjected to hydrogenation at room temperature and 50–60 psi of hydrogen pressure for a period of 8–12 hours. The progress of the reaction was monitored by TLC. After completion of the reaction, the catalyst was filtered off and the solvent was removed under reduced pressure to afford the compound of the formula (13) (28–29 g, 97–98%).

Step-vii:

Preparation of S(−)-ethyl 3-[4-[2-(phenoxazin-10-yl)ethoxy]phenyl]-2-ethoxypropionate of the formula (16):

A mixture of S(−)-ethyl 2-ethoxy-3-(4-hydroxyphenyl)propionate of the formula (13) (25 g) obtained according to the procedure described in step (vi) above, the mesylate of the formula (15) (32 g), potassium carbonate (36 g) and toluene (250 ml) was refluxed for a period of 15–20 hours. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title compound of the formula (16) (46–47 g, 98–99%), as an oily material.

Step-viii:

Preparation of S(−)-3-[4-[2-(phenoxazin-10-yl)ethoxy]phenyl]-2-ethoxypropanoic acid of the Formula (1):

To a mixture of S(−)-ethyl 3-[4-[2-(phenoxazin-10-yl)ethoxy]phenyl]-2-ethoxy-propionate of the formula (16) (45 g) obtained according to the procedure described in step (vii) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (16), the reaction mass was diluted with water (225 ml) and washed with toluene to remove the impurities. The aqueous layer was acidified with dilute hydrochloric acid and extracted with toluene. Combined organic extracts were washed with, water and concentrated under reduced pressure to half the volume and treated with activated charcoal. Filtration of the charcoal followed by concentration of toluene to ~50 ml and precipitation with pet. ether afforded the title compound of the formula (1) (38–39 g, 90–92%).

EXAMPLE 6

Step-i:

Preparation of 4-benzyloxybenzaldehyde of the Formula (8):

4-Hydroxybenzaldehyde of the formula (7) (100 g), potassium carbonate (226 g) and dimethylformamide (500 ml) were taken in a reaction flask and stirred for 15 minutes. Benzylchloride (114 g) was then added at room temperature and the reaction mass was stirred at the same temperature for a period of 8–10 h. The progress of the reaction was monitored by TLC. After completion of the reaction, the reaction mixture was dumped into ice water and extracted with toluene. The combined organic extracts were washed with 10% aq. sodium hydroxide solution followed by water. The solvent was removed under reduced pressure and the resulting residue was triturated with pet ether to afford the title compound of the formula (8) (160–165 g, 93–95%).

Step-ii:

Preparation of ethyl-2,3-epoxy-3-(4-benzyloxyphenyl)propionate of the Formula (9):

A mixture of 4-benzyloxybenzaldehyde of the formula (8) (100 g) obtained according to the procedure described in step (i) above, potassium carbonate (260 g), dimethylformamide (500 ml) ethylchloroacetate (86 g) and tetrabutylammonium bromide (1 g) was stirred at room temperature for a period of 30–45 h. The progress of the reaction was monitored by TLC. After completion of the reaction, the reaction mixture was dumped into ice water and stirred for 5–10 minutes. The solid thus obtained was filtered, washed with water and dried to afford the title compound of the formula (9) (126–129 g. 90–92%).

Step-iii:

Preparation of racemic ethyl 2-hydroxy-3-(4-benzyloxyphenyl)propionate of the Formula (10):

A mixture of ethyl-2,3-epoxy-3-(4-benzyloxyphenyl)propionate of the formula (9) (125 g) obtained according to the procedure described in step (ii) above, 5% Pd/C (12.5 g) and 1,4-dioxane (750 ml) was hydrogenated at room temperature at 5–10 psi of hydrogen pressure for a period of 10–15 h. The progress of the reaction was monitored by TLC. After completion of the reaction, the catalyst was filtered and the solvent was removed under reduced pressure to afford the title compound of the formula (10) (100–105 g, 80–83%).

Step-iv:

Preparation of racemic ethyl 2-ethoxy-3-(4-benzyloxyphenyl)propionate of the Formula (12a):

To a slurry of sodium hydride (60% suspension in oil, 7.5 g) and dimethyl formamide (70 ml) was added a solution of the racemic ethyl 2-hydroxy-3-(4-benzyloxyphenyl(propionate of the formula (10) (40 g) obtained according to the procedure described in step (iii) above in dimethylformamide (105 ml) at 5–10° C. over a period of 15–30 minutes. The temperature was allowed to attain room temperature and maintained at the same temperature for 1–3 h. Ethyl iodide (36 g) was added slowly by maintaining the temperature at 25–30° C. over a period of 2–3 h. The progress of the reaction was monitored by TLC. After completion of the reaction, the reaction mixture was dumped into ice water and extracted with toluene. The combined organic extracts were washed with water and the solvent was removed under reduced pressure to afford the title compound of the formula (12a) (47–48 g, 98–99%).

Step-v:

Preparation of racemic ethyl 2-ethoxy-3-(4-hydroxyphenyl)propionate of the Formula (13a):

A mixture of racemic ethyl 2-ethoxy-3-(4-benzyloxyphenyl)propionate of the formula (12a) (40 g) obtained according to the procedure described in step (iv) above, 5% Pd/C (8 g) and tetrahydrofuran (120 ml) was subjected to hydrogenation at room temperature and 50–60 psi of hydrogen pressure for a period of 8–12 h. The progress of the reaction was monitored by TLC. After completion of the reaction, the catalyst was filtered off and the solvent was removed under reduced pressure to afford the title compound of the formula (13a) (28–29 g, 97–98%).

Step-vi:

Preparation of Racemic Ethyl 3-[4-[2-(phenoxazin-10-yl)ethoxy]phenyl]-2-ethoxypropionate of the Formula (4):

A mixture of racemic ethyl 2-ethoxy-3-(4-hydroxyphenyl)propionate of the formula (13a) (25 g) obtained according to the procedure described in step (v) above, the mesylate of the formula (15) (32 g), potassium carbonate (36 g) and toluene (250 ml) was refluxed for a period of 15–20 h. The progress of the reaction was monitored by TLC. After completion of the reaction, the reaction mass was dumped into ice water and extracted with toluene. The combined organic extracts were washed with water and concentrated under vacuum to afford racemic ester of the formula (4) (46–47 g, 98–99%) as an oily material.

Step-vii:

Preparation of racemic 3-[4-[2-(phenoxazin-10-yl)ethoxy]phenyl]-2-ethoxypropanoic acid of the Formula (5):

To a mixture of racemic ethyl 3-[4-[2-(phenoxazin-10-yl)ethoxy]phenyl]-2-ethoxypropionate of the formula (4) (45 g) obtained according to the procedure described in step (vi) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (4), the reaction mass was diluted with water (225 ml) and washed with toluene to remove the impurities. The aqueous layer was acidified with dilute hydrochloric acid and extracted with toluene. The combined organic extracts were washed with water and concentrated under reduced pressure to half the volume and treated with activated charcoal. Filtration of the charcoal followed by concentration of toluene to ~50 ml and precipitation with pet. ether afforded racemic acid of the formula (5) as an off-white to white solid, which was filtered and dried at room temperature (~30° C.), (38–39 g 90–92%).

Step-viii:

Preparation of S(−)-3-[-4-[2-(phenoxazin-10-yl)ethoxy]phenyl]-2-ethoxypropanoic acid of the Formula (1):

To a solution of racemic 3-[4-[2-(phenoxazin-10-yl)ethoxy]phenyl]-2-ethoxypropanoic acid of the formula (5) (35 g) obtained according to the procedure described in step (vii) above in ethyl acetate (525 ml) was added n-octylglucosamine (24.5 g) and the mixture was stirred at room temperature for a period of 2–4 hours. The solid thus obtained was filtered and the acid was regenerated after acidification to afford S(−)-α-ethoxy acid of the formula (1) (15–17 g, 44–47%). The R(+)-α-ethoxy acid obtained from the mother liquor was racemised and mixed with subsequent batches for resolution. The overall yield obtained by several such reprocesses was ~90–95%.

EXAMPLE 7

Step-i:

Preparation of 5-(4-hydroxybenzal)hydantoin of the Formula (18):

A mixture of 4-hydroxybenzaldehyde (100 g, 0.819 M), hydantoin (90 g, 0.9 M) and piperidine (165 ml) was heated to 130° C. for 1 h. The progress of the reaction was monitored by TLC. After completion of the reaction, the reaction mixture was cooled to 60° C. and 3.2l water was added. The reaction mixture was acidified with 12N HCl. The precipitated solid was filtered and washed with cold water to yield the title compound of the formula (18) (147 g, 88%), (Org. Syn. Vol. V., pp627).

Step-ii:

Preparation of 4-hydroxyphenylpyruvic acid of the Formula (19):

To 5-(4-hydroxybenzal)hydantoin of the formula (18) (7.5 g, 0.367 M), obtained according to the procedure described in step (i) above, sodium hydroxide (20%, 2.1l) was added slowly. The reaction mixture was heated to 160–170° C. for 3 h. The progress of the reaction was monitored by TLC. After completion of the reaction, the reaction mixture was cooled to 0–5° C. and acidified with 12N HCl. The reaction mixture was basified with sodium bicarbonate and washed with diethylether. Aqueous layer was acidified with 12 N HCl and extracted with diethylether. The combined diethyl layer was dried to yield crude compound. The crude compound (10 g) was recrystallised with aqueous hydrochloric acid to yield the title compound of the formula (19) (6.5 g, 65%).

Step-iii:

Preparation of racemic ethyl 2-hydroxy-3-(4-hydroxyphenyl)propionate of the Formula (20):

4-Hydroxyphenylpyruvic acid of the formula (19) (30 g, 0.166 M) obtained according to the procedure described in step (ii) above was dissolved in ethylacetate (500 ml) and 5% Pd—C (5.0 g) was added and hydrogenated at 60 psi—hydrogen pressure. The progress of the reaction was monitored by TLC. After completion of the reaction, the catalyst was filtered and the solvent was evaporated to yield racemic 2-hydroxy-3-(4-hydroxyphenyl)propionic acid (28 g; 93%).

Racemic 2-hydroxy-3-(4-hydroxyphenyl)propionic acid (30 g, 0.164 M) obtained according to the procedure described above dissolved in 5% ethanolic sulphuric acid (600 ml) was refluxed for 6 h. The reaction mixture was cooled to room temperature and concentrated. The resulting residue was diluted with ethylacetate and washed with water. The ethylacetate layer was separated and evaporated to yield racemic ethyl-2-hydroxy-3-(4-hydroxyphenyl)propionate of the formula (20) (24 g, 75%).

Step-iv:

Preparation of racemic ethyl 2-hydroxy-3-(4-benzyloxyphenyl)propionate of the Formula (10):

Racemic ethyl-2-hydroxy-3-(4-hydroxyphenyl)propionate of the formula (20) (5 g, 0.025M), obtained according to the procedure described in step (iii) above, benzylchloride (3.54 g, 0.028M), potassium carbonate (8.0 g, 0.058M) were taken in dethylformamide (100 ml) and stirred at room temperature for 12 h. The progress of the reaction was monitored by TLC. After completion of the reaction, ice cold water was added to the reaction mixture and extracted with diethylether. The combined diethylether extracts were evaporated to afford racemic ethyl 2-hydroxy-3-(4-benzyloxyphenyl)propionate of the formula (10) (5.5 g, 76%).

Step-v:

Preparation of S(−)-2-hydroxy-3-(4-benzyloxyphenyl)propionic acid of the Formula (11):

A mixture of racemic ethyl 2-hydroxy-3-(4-benzyloxyphenyl)propionate of the formula (10) (100 g) obtained according to the procedure described in step (iv) above and 10% aq. sodium hydroxide solution (500 ml) was stirred at room temperature for a period of 1–2 h. The progress of the reaction was monitored by TLC After completion of the reaction, the reaction mixture was acidified with dil. hydrochloric acid at 15–20° C. and the solid thus obtained was filtered and washed with water to afford racemic 2-hydroxy acid (72–77 g, 80–85%).

To a solution of racemic ethyl 2-hydroxy-3-(4-benzyloxyphenyl)propionic acid (75 g) obtained according to the procedure described above in ethylacetate (1.1 L) was added R(+)-α-methylbenzylamine (33 g) and the mixture was stirred at room temperature for a period of 2–4 h. The solid thus obtained was filtered and the acid was regenerated after acidification to afford S(−)-2-hydroxy-3-(4benzyloxyphenyl)propionic acid of the formula (11), (33–35 g, 44–47%). The R(+)-α-hydroxy acid obtained from the mother liquor was racemised and mixed with subsequent batches for resolution The overall yield obtained by several such reprocesses was ~90–95%.

Step-vi:

Preparation of S(−)-ethyl 2-ethoxy-3-(4-benzyloxyphenyl)propionate of the Formula (12):

To a slurry of sodium hydride (60% suspension in oil, 13 g) and dimethyl formamide (70 ml) was added a solution of S(−)-2-hydroxy-3-(4-benzyloxyphenyl) propionic acid of the formula (11) (35 g) obtained according to the procedure described in step (v) above, in dimethylformamide (105 ml) at 5–10° C. over a period of 15–30 minutes. The temperature was allowed to attain room temperature and maintained at the sake temperature for 1–3 hours. Ethyl iodide (62 g) was added slowly by maintaining the temperature at 25–30° C. over a period of 2–3 hours. The progress of the reaction was monitored by TLC. After completion of the reaction, the reaction mixture was dumped into ice water and extracted with toluene. The combined organic extracts were washed with water and the solvent was removed under reduced pressure to afford the title compound of the formula (12) (41–42 g, 98–99%).

Step-vii:

Preparation of S(−)-ethyl 2-ethoxy-3-(4-hydroxyphenyl)propionate of the Formula (13):

A mixture of S(−)-ethyl 2-ethoxy-3-(4-benzyloxyphenyl)propionate of the formula (12) (40 g) obtained according to the procedure described in step (vi) above, 5% Pd/C catalyst (8 g) and tetrahydrofuran (120 ml) was subjected to hydrogenation at room temperature and 50–60 psi of hydrogen pressure for a period of 8–12 hours. The progress of the reaction was monitored by TLC. After completion of the reaction, the catalyst was filtered off and the solvent was removed under reduced pressure to afford the title compound of the formula (13) (28–29 g, 97–98%).

Step-viii:

Preparation of S(−)-ethyl 3-[4-[2-(phenoxazin-10-yl)ethoxy]phenyl]-2-ethoxypropionate of the Formula (16):

A mixture of S(−)-ethyl 2-ethoxy-3-(4-hydroxyphenyl)propionate of the formula (13) (25 g) obtained according to the procedure described in step (vii) above, the mesylate of the formula (15) (32 g), potassium carbonate (36 g) and toluene (250 ml) was refluxed for a period of 15–20 hours. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title compound of the formula (16) (46–47 g, 98–99%), as an oily material.

Step-ix:

Preparation of S(−)-3-[4-[2-(phenoxazin-10-yl)ethoxy]phenyl]-2-ethoxypropanoic acid of the Formula (1):

To a mixture of S(−)-ethyl 3-[4-[2-(phenoxazin-10-yl)ethoxy]phenyl]-2-ethoxypropionate of the formula (16) (45 g) obtained according to the procedure described in step (viii) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (16), the reaction mass was diluted with water,(225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded the title compound of the formula (1) (38–39 g, 90–92%).

EXAMPLE 8

Step-i:

Preparation of 5(4-hydroxybenzal)hydantoin of the Formula (18):

A mixture of 4-hydroxybenzaldehyde (100 g, 0.819 M),-hydantoin (90 g, 0.9 M) and piperidine (165 ml) was heated to 130° C. for 1 h. The progress of the reaction was monitored by TLC. After completion of the reaction, the reaction mixture was cooled to 60° C. and 3.21 water was added. The reaction mixture was acidified with 12N HCl. The precipitated solid was filtered and washed with cold water to yield the title compound of the formula (18) (147 g, 88%), (*Org. Syn. Vol. V.*, pp627).

Step-ii:

Preparation of 4-hydroxyphenylpyruvic Acid of the Formula (19):

To 5-(4-hydroxybenzal)hydantoin of the formula (18) (7.5 g, 0.367 M), obtained according to the procedure described in step (i) above, sodium hydroxide (20%, 2.11) was added slowly. The reaction mixture was heated to 160–170° C. for 3 h. The progress of the reaction was monitored by TLC. After completion of the reaction, the reaction mixture was cooled to 0–5° C. and acidified with 12N HCl. The reaction mixture was basified with sodium bicarbonate and washed with diethylether. Aqueous layer was acidified with 12 N HCl and extracted with diethylether. The combined diethyl layer was dried to yield crude compound. The crude compound (10 g) was recrystallised with aqueous hydrochloric acid to yield the title compound of the formula (19) (6.5 g, 65%).

Step-iii:

Preparation of racemic ethyl 2-hydroxy-3-(4-hydroxyphenyl)propionate of the Formula (20):

4-Hydroxyphenylpyruvic acid of the formula (19) (30 g, 0.166 M) obtained according to the procedure described in step (ii) above was dissolved in ethanol (500 ml) and 5% Pd—C (5.0 g) was added and hydrogenated at 60 psi—hydrogen pressure. The progress of the reaction was monitored by TLC. After completion of the reaction, the catalyst was filtered and the solvent was evaporated to yield racemic ethyl-2-hydroxy-3-(4-hydroxyphenyl)propionate of the formula (20) (28 g, 93%).

Step-iv:

Preparation of racemic ethyl-2-hydroxy-3-(4-benzyloxyphenyl)propionate of the Formula (16):

Racemic ethyl 2-hydroxy-3-(4-hydroxyphenyl)propionate of the formula (20) (5 g, 0.025M), obtained according to the procedure described in step (iii) above, benzylchloride (3.54 g, 0.028M), potassium carbonate (8.0 g, 0.058M) were taken in dimethylformamide (100 ml) and stirred at room temperature for 12 h. The progress of the reaction was monitored by TLC. After completion of the reaction, ice cold water was added to the reaction mixture and extracted with diethylether. The combined diethylether extracts were evaporated to afford racemic ethyl 2-hydroxy-3-(4-benzyloxyphenyl)propionate of the formula (10) (5.5 g, 76%).

Step-v:

Preparation of S(−)-2-hydroxy-3-(4-benzyloxyphenyl) propionic acid of the formula (11):

A mixture of racemic ethyl 2-hydroxy-3-(4-benzyloxyphenyl)propionate of the formula (10) (100 g) obtained according to the procedure described in step (iv) above and 10% aq. sodium hydroxide solution (500 ml) was stirred at room temperature for a period of 1–2 h. The progress of the reaction was monitored by TTC. After completion of the reaction, the reaction mixture was acidified with dil. hydrochloric acid at 15–20° C. and the solid thus obtained was filtered and washed with water to afford racemic 2-hydroxy acid (72–77 g, 80–85%).

To a solution of racemic ethyl 2-hydroxy-3-(4-benzyloxyphenyl)propionic acid (75 g) obtained according to the procedure described above in ethylacetate (1.1 L) was added R(+)-α-methylbenzylamine (33 g) and the mixture was stirred at room temperature for a period of 2–4 h. The solid thus obtained was filtered and the acid was regenerated after acidification to afford S(−)-2-hydroxy-3-(4-benzyloxyphenyl)propionic acid of the formula (11), (33–35 g, 44–47%). The R(+)-α-hydroxy acid obtained from the mother liquor was racemised and mixed with subsequent batches for resolution. The overall yield obtained by several such reprocesses was ~90–95%.

Step-vi:

Preparation of S(−)-ethyl 2-ethoxy-3-(4-benzyloxyphenyl)propionate of the Formula (12):

To a slurry of sodium hydride (60% suspension in oil, 13 g) and dimethyl formamide (70 ml) was added a solution of S(−)-2-hydroxy-3-(4-benzyloxyphenyl)propionic acid of the formula (11) (35 g) obtained according to the procedure described in step (v) above, in dimethylformamide (105 ml) at 5–10° C. over a period of 15–30 minutes. The temperature was allowed to attain room temperature and maintained at the same temperature for 1–3 hours. Ethyl iodide (62 g) was added slowly by maintaining the temperature at 25–30° C. over a period of 2–3 hours. The progress of the reaction was monitored by TLC. After completion of the reaction, the reaction mixture was dumped into ice water and extracted with toluene. The combined organic extracts were washed with water and the solvent was removed under reduced pressure to afford the title compound of the formula (12) (41–42 g, 98–99%).

Step-vii:

Preparation of S(−)-ethyl 2-ethoxy-3-(4-hydroxyphenyl)propionate of the Formula (13):

A mixture of S(−)-ethyl 2-ethoxy-3-(4-benzyloxyphenyl)propionate of the formula (12) (40 g) obtained according to the procedure described in step (vi) above, 5% Pd/C catalyst (8 g) and tetrahydrofuran (120 ml) was subjected to hydrogenation at room temperature and 50–60 psi of hydrogen pressure for a period of 8–12 hours. The progress of the reaction was monitored by TC. After completion of the reaction, the catalyst was filtered off and the solvent was removed under reduced pressure to afford the title compound of the formula (13) (28–29 g, 97–98%).

Step-viii:

Preparation of S(−)-ethyl 3-[4-[2-(phenoxazin-10-yl)ethoxy]phenyl]-2-ethoxypropionate of the Formula (16):

A mixture of S(−)-ethyl 2-ethoxy-3-(4-hydroxyphenyl)propionate of the formula (13) (25 g) obtained according to the procedure described in step (vii) above, the mesylate of the formula (15) (32 g), potassium carbonate (36 g) and toluene (250 ml) was refluxed for a period of 15–20 hours. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title compound of the formula (16) (46–47 g, 98–99%), as an oily material.

Step-ix:

Preparation of S(−)-3-[4-[2-(phenoxazin-10-yl)ethoxy]phenyl]-2-ethoxypropanoic acid of the Formula (1):

To a mixture of S(−)-ethyl 3-[4-[2-(phenoxazin-10-yl)ethoxy]phenyl]-2-ethoxypropionate of the formula (16) (45 g) obtained according to the procedure described in step (viii) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (16), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded the title compound of the formula (1) (38–39 g, 90–92%).

EXAMPLE 9

Step-i:

Preparation of 5-(4-hydroxybenzal)hydantoin of the Formula (18):

A mixture of 4-hydroxybenzaldehyde (100 g, 0.819 M), hydantoin (90 g, 0.9 M) and piperidine (165 ml) was heated to 13° C. for 1 h. The progress of the reaction was monitored by TLC. After completion of the reaction, the reaction mixture was cooled to 60° C. and 3.21 water was added. The reaction mixture was acidified with 12N HCl. The precipitated solid was filtered and washed with cold water to yield the title compound of the formula (18) (147 g, 88%), (*Org. Syn. Vol. V.*, pp627).

Step-ii:

Preparation of 4-hydroxphenylpyruvic acid of the Formula (19):

To 5-(4-hydroxybenzal)hydantoin of the formula (18) (7.5 g, 0.367 M), obtained according to the procedure described in step (i) above, sodium hydroxide (20%, 2.11) was added slowly. The reaction mixture was heated to 160–170° C. for 3 h. The progress of the reaction was monitored by TLC. After completion of the reaction, the reaction mixture was cooled to 0–5° C. and acidified with 12N HCl. The reaction mixture was basified with sodium bicarbonate and washed with diethylether. Aqueous layer was acidified with 12 N HCl and extracted with diethylether. The combined diethyl layer was dried to yield crude compound. The crude compound (10 g) was recrystallised with aqueous hydrochloric acid to yield the title compound of the formula (19) (6.5 g, 65%).

Step-iii:

Preparation of racemic ethyl 2-hydroxy-3-(4-hydroxyphenyl)propionate of the Formula (20):

4-Hydroxyphenylpyruvic acid of the formula (19) (30 g, 0.166 M) obtained according to the procedure described in step (ii) above was dissolved in ethylacetate (500 ml) and 5% Pd—C (5.0 g) was added and hydrogenated at 60 psi—hydrogen pressure. The progress of the reaction was monitored by TLC. After completion of the reaction, the catalyst was filtered and the solvent was evaporated to yield racemic 2-hydroxy-3-(4-hydroxyphenyl)propionic acid (28 g; 93%).

Racemic 2-hydroxy-3-(4-hydroxyphenyl)propionic acid (30 g, 0.164 M) obtained according to the procedure described above dissolved in 5% ethanolic sulphuric acid (600 ml) was refluxed for 6 h. The reaction mixture was cooled to room temperature and concentrated. The resulting residue was diluted with ethylacetate and washed with water. The ethylacetate layer was separated and evaporated to yield racemic ethyl 2-hydroxy-3-(4-hydroxyphenyl)propionate of the formula (20) (24 g, 75%).

Step-iv:

Preparation of racemic ethyl 2-hydroxy-3-(4-benzyloxyphenyl)propionate of the Formula (10):

Racemic ethyl 2-hydroxy-3-(4-hydroxyphenyl)propionate of the formula (20) (5 g, 0.025M), obtained according to the procedure described in step (iii) above, benzylchloride (3.54 g, 0.028M), potassium carbonate (8.0 g, 0.058M) were taken in dimethylformamide (100 ml) and stirred at room temperature for 12 h. The progress of the reaction was monitored by TLC. After completion of the reaction. ice cold water was added to the reaction mixture and extracted with diethylether. The combined diethylether extracts were evaporated to afford racemic ethyl 2-hydroxy-3-(4-benzyloxyphenyl)propionate of the formula (10) (5.5 g, 76%).

Step-v:

Preparation of racemic ethyl 2-ethoxy-3-(4-benzyloxyphenyl)propionate of the Formula (12a):

To a slurry of sodium hydride (60% suspension in oil, 7.5 g) and dimethyl formamide (70 ml) was added a solution of the racemic ethyl 2-hydroxy-3-(4-benzyloxyphenyl)propionate of the formula (10) (40 g) obtained according to the procedure described in step (iv) above in dimethylformamide (105 ml) at 5–10° C. over a period of 15–30 minutes. The temperature was allowed to attain room temperature and maintained at the same temperature for 1–3 h Ethyl iodide (36 g) was added slowly by maintaining the temperature at 25–30° C. over a period of 2–3 hours. The progress of the reaction was monitored by TLC. After completion of the reaction, the reaction mixture was dumped into ice water and extracted with toluene. The combined organic extracts were washed with water and the solvent was removed under reduced pressure to afford the title compound of the formula (12a) (47–48 g, 98–99%).

Step-vi:

Preparation of racemic ethyl 2-ethoxy-3-(4-hydroxyphenyl)propionate of the Formula (13a):

A fixture of racemic ethyl 2-ethoxy-3-(4-benzyloxyphenyl)propionate of the formula (12a) (40 g) obtained according to the procedure described in step (v) above, 5% Pd/C catalyst (8 g) and tetrahydrofuran (120 ml) was subjected to hydrogenation at room temperature and 50–60 psi of hydrogen pressure for a period of 8–12 h. The progress of the reaction was monitored by TLC. After completion of the reaction, the catalyst was filtered off and the solvent was removed under reduced pressure to afford the title compound of the formula (13a) (28–29 g, 97–98%).

Step-vii:

Preparation of racemic ethyl 3-[4-[2-(phenoxazin-10-yl)ethoxy]phenyl]-2-ethorypropionate of the Formula (4):

A mixture of racemic ethyl 2-ethoxy-3-(4-hydroxyphenyl)propionate of the formula (13a) (25 g) obtained according to the procedure described in step (vi) above, the mesylate of the formula (15) (32 g), potassium carbonate (36 g) and toluene (250 ml) was refluxed for a period of 15–20 h. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford racemic ester of the formula (4) (46–47 g, 98–99%) as an oily material.

Step-viii:

Preparation of racemic 3-[4-[2-(phenoxazin-10-yl)ethoxy]phenyl]-2-ethoxypropanoic Acid of the Formula (5):

To a mixture of racemic ethyl 3-[4-[2-(phenoxazin-10-yl)ethoxy]phenyl]-2-ethoxypropionate of the formula (4) (45 g) obtained according to the procedure described in step (vii) and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (4), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet ether afforded racemic acid of the formula (5) as an off-white to white solid, which was filtered and dried at room temperature (~30° C.), (38–39 g, 90–92%).

Step-ix:

Preparation of S(–)-3-[4-[2-(phenoxazin-10-yl)ethoxy]phenyl]-2-ethoxypropanoic acid of the Formula (1):

To a solution of racemic 3-[4-[2-(phenoxazin-10-yl)ethoxy]phenyl]-2-ethoxypropanoic acid of the formula (5) (35 g) obtained according to the procedure described in step (viii) above in ethyl acetate (525 ml) was added R(+)-α-methyl-benzylamine (10 g) and the mixture was stirred at room temperature for a period of 2–4 h. The solid thus obtained was filtered and the acid was regenerated after acidification to afford (15–17 g, 44–47%) of S(–)-α-ethoxy acid of the formula (1). The R(+)-α-ethoxy acid obtained from the mother liquor was racemized and mixed with subsequent batches for resolution. The overall yield obtained by several such reprocesses was ~90–95%.

EXAMPLE 10

Step-i:

Preparation of 5-(4-hydroxybenzal)hydantoin of the Formula (18):

A mixture of 4-hydroxybenzaldehyde (100 g, 0.819 M), hydantoin (90 g, 0.9 M) and piperidine (165 ml) was heated to 130° C. for 1 h. The progress of the reaction was monitored by TLC. After completion of the reaction, the reaction mixture was cooled to 60° C. and 3.21 water was added. The reaction mixture was acidified with 12N HCl. The precipitated solid was filtered and washed with cold water to yield the title compound of the formula (18) (147 g, 88%), (*Org. Syn. Vol. V.*, pp627).

Step-ii:

Preparation of 4-hydroxyphenylpyruvic acid of the Formula (19):

To 5-(4-hydroxybenzal)hydantoin of the formula (18) (75 g, 0.367 M), obtained according to the procedure described in step (i) above, sodium hydroxide (20%, 2.11) was added slowly. The reaction mixture was heated to 160–170° C. for 3 h. The progress of the reaction was monitored by TLC. After completion of the reaction, the reaction mixture was cooled to 0–5° C. and acidified with 12N HCl. The reaction mixture was basified with sodium bicarbonate and washed with diethylether. Aqueous layer was acidified with 12 N HCl and extracted with diethylether. The combined diethyl layer was dried to yield crude compound. The crude compound (10 g) was recrystallized with aqueous hydrochloric acid to yield the title compound of the formula (19) (6.5 g, 65%).

Step-iii:

Preparation of racemic ethyl 2-hydroxy-3-(4-hydroxyphenyl)propionate of the Formula (20):

4-Hydroxyphenylpyruvic acid of the formula (19) (30 g, 0.166 M) obtained according to the procedure described in step (ii) above was dissolved in ethanol (500 ml) and 5% Pd—C (5.0 g) was added and hydrogenated at 60 psi—hydrogen pressure. The progress of the reaction was monitored by TLC. After completion of the reaction, the catalyst was filtered and the solvent was evaporated to yield racemic ethyl 2-hydroxy-3-(4-hydroxyphenyl)propionate of the formula (20) (28 g; 93%).

Step-iv:

Preparation of racemic ethyl 2-hydroxy-3-(4-benzyloxyphenyl)propionate of the Formula (10):

Racemic ethyl-2-hydroxy-3-(4-hydroxyphenyl)propionate of the formula (20) (5 g, 0.025M), obtained according to the procedure described in step (iii) above, benzylchloride (3.4 g, 0.028M), potassium carbonate (8.0 g, 0.058M) were taken in dimethylformamide (100 ml) and stirred at room temperature for 12 h. The progress of the reaction was monitored by TLC. After completion of the reaction, ice cold water was added to the reaction mixture and extracted with diethylether. The combined diethylether extracts were evaporated to afford racemic ethyl 2-hydroxy-3-(4-benzyloxyphenyl)propionate of the formula (10) (5.5 g, 76%).

Step-v:

Preparation of racemic ethyl 2-ethoxy-3-(4-benzyloxyphenyl)propionate of the Formula (12a):

To a slurry of sodium hydride (60% suspension in oil, 7.5 g), and dimethyl formamide (70 ml) was added a solution of the racemic ethyl-2-hydroxy-3-(4-benzyloxyphenyl)propionate of the formula (10) (40 g) obtained according to the procedure described in step (iv) above in dimethylformide (105 ml) at 5–10° C. over a period of 15–30 minutes. The temperature was allowed to attain room temperature and maintained at the same temperature for 1–3 h. Ethyl iodide (36 g) was added slowly by maintaining the temperature at 25–30° C. over a period of 2–3 hours. The progress of the reaction was monitored by TLC. After completion of the reaction, the reaction mixture was dumped into ice water and extracted with toluene. The combined organic extracts were washed with water and the solvent was removed under reduced pressure to afford racemic 2-ethoxy ethyl ester of the formula (12a) (47–48 g, 98–99%).

Step-vi:

Preparation of racemic ethyl 2-ethoxy-3-(4-hydroxyphenyl)propionate of the Formula (13a):

A mixture of racemic ethyl 2-ethoxy-3-(4-benzyloxyphenyl)propionate of the formula (12a) (40 g) obtained according to the procedure described in step (v) above, 5% Pd/C catalyst (8 g) and tetrahydrofuran (120 ml) was subjected to hydrogenation at room temperature and 50–60 psi of hydrogen pressure for a period of 8–12 h. The progress of the reaction was monitored by TLC. After completion of the reaction, the catalyst was filtered off and the solvent was removed under reduced pressure to afford the title compound of the formula (13a) (28–29 g, 97–98%).

Step-vii:

Preparation of racemic ethyl 3-[4-[2(phenoxazin-10-yl)ethoxy]phenyl]-2-ethoxypropionate of the Formula (4):

A mixture of racemic ethyl 2-ethoxy-3-(4-hydroxyphenyl)propionate of the formula (13a) (25 g) obtained according to the procedure described in step (vi) above, the mesylate of the formula (15) (32 g), potassium carbonate (36 g) and toluene (250 ml) was refluxed for a period of 15–20 h. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford racemic ester of the formula (4) (46–47 g, 98–99%) as an oily material.

Step-viii:

Preparation of racemic 3-[4-[2-(phenoxazin-10-yl)ethoxy]phenyl]-2-ethoxypropanoic acid of the Formula (5):

To a mixture of racemic ethyl 3-[4-[2-(phenoxazin-10-yl)ethoxy]phenyl]-2-ethoxypropionate of the formula (4) (45 g) obtained according to the procedure described in step (vii) and methanol (225 ml) was added aqueous 10% sodium hydroxide solution (225 ml) slowly at room temperature over a period of 10–15 minutes; The reaction mixture was stirred at the same temperature for a period of 2–4 h. The progress of the reaction was monitored by TLC. After the complete hydrolysis of the compound of the formula (4), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded racemic acid of the formula (5) as an off-white to white solid which was filtered and dried at room temperature (~30° C.), (38–39 g, 90–92%).

Step-ix:

Preparation of (2S), N(1S)-3-[4-[2-(phenoxazin-10-yl)ethoxy]phenyl]-2-ethoxy-N-(2-hydroxy-1-phenylethyl)propanamide of the Formula (6):

Racemic 3-[4-[2-(phenoxazin-10-yl)ethoxy]phenyl]-2-ethoxypropanoic acid of the formula (5) (55 g, 0.13 M) obtained according to the procedure described in step (viii) above, S(+)-2-phenylglycinol (18 g, 0.13M) and 1-hydroxybenzothiazole (18 g, 0.13M) were dissolved in ethyl acetate (800 ml). Dicyclohexylcarbodiimide (29.5 g, 0.14M) dissolved in ethyl acetate (200 ml) was added to the above reaction mixture and stirred for 3 h. The progress of the reaction was monitored by TLC. After completion of the reaction, dicyclohexylurea was filtered and ethyl acetate layer was washed with water and evaporated to give the crude compound. The crude compound was dissolved in ethyl acetate and precipitated with pet. ether to yield the title compound of the formula (6) (29 g, 82%).

Step-x:

Preparation of S(−)-3-[4-[2-(phenoxazin-10-yl)ethoxy]phenyl]-2-ethoxypropanoic acid of the Formula (1):

(2S), N(1S)-3-[4-[2-(phenoxazin-10-yl)ethoxy]phenyl]-2-ethoxy-N-2-hydroxy-1-phenylethyl)propanamide of the formula (6) (50 g, 0.09 M) obtained according to the procedure described in step (ix) above, dissolved in 1,4-dioxane (1650 ml) was added to 3M sulfuric acid (2.51) and refluxed for 16 h. The progress of the reaction was monitored by TLC. After completion of the reaction, the reaction mixture was extracted with ethyl acetate. The combined organic extracts were washed with water, bicarbonate and 1N hydrochloric acid and concentrated to yield the title compound of the formula (1) (31 g, 79%).

EXAMPLE 11

Step-i:
Preparation of (S)-2-amino-3-(4-benzyloxyphenyl)propionic acid of the Formula (22):

To a solution of L-tyrosine of the formula (21) (18.1 g) in 2N NaOH solution (115 ml), copper sulphate solution (12.5 g of $CuSO_4$ in 50 ml of water) was added and heated at 60° C. for 1.5 h. The reaction mixture was cooled to room temperature and methanol (350 ml) and 2N NaOH (12.5 ml) was added and then benzyl bromide (12 ml) was added drop wise. The reaction mass was allowed to warm to room temperature. The precipitate was filtered and washed to give the title compound as white to off-white solid (18.5 g, 66.8%) (Ref. Bodansky & Bodansky pp50).

Step-ii:
Preparation of S(−)-2-hydroxy-3-(4-benzyloxyphenyl) propionic acid of the Formula (11'):

To a solution of (S)-2-amino-3-(4-benzyloxyphenyl)propionic acid of the formula (22) (10 g) obtained according to the procedure described in step (i) above in glacial acetic acid (200 ml) and chloroform (50 ml) at 0–5° C., isoamyl nitrite (13.51 ml) was added slowly in 1 h time and stirred for further 2 h at room temperature. The progress of the reaction was monitored by TLC. After completion of the reaction, the reaction mixture was diluted with water and the compound was extracted into chloroform. The combined organic layers were washed with water and concentrated to give (S)-2-acetoxy acid as white solid (13 g, 78%).

A mixture of (S)-2-acetoxy-3-(4-benzyloxyphenyl) propionic acid (5.0 g) obtained according to the procedure described above and 10% as sodium hydroxide solution (40 ml) was stirred at room temperature for a period of 8 h. The progress of the reaction was monitored by TLC. After completion of the reaction, the reaction mixture was diluted with water, acidified with dil HCl to pH-3 and the compound was extracted with chloroform, evaporation of the solvent gave the title compound of the formula (11') as white solid (3.7 g, 85.4%).

Step-iii:
Preparation of S(−)-ethyl 2-ethoxy-3-(4-benzyloxyphenyl)propionate of the Formula (12):

To a stirred solution of S(−)-2-hydroxy-3-(4-benzyloxyphenyl)propionic acid of the formula (11') (2 g) obtained according to the procedure described in step (ii) above in DMSO (30 ml) at room temperature, KOH (3.32 g) was added and stirred for 1 h and than ethyl iodide (4.5 g) was added and stirred for further 2 h at room temperature. The progress of the reaction was monitored by TLC. After completion of the reaction the reaction mixture was extracted with toluene (30 ml). The combined organic extracts were washed with water, dried and concentrated to yield the title compound of the formula (12) as syrupy liquid, (2.9 g, 87%).

Step-iv:
Preparation of S(−)-ethyl 2-ethoxy-3-(4-hydroxyphenyl)propionate of the Formula (13):

A solution of S(−)-ethyl 2-ethoxy-3-(4-benzyloxyphenyl) propionate of the formula (12) (12 g) obtained according to the procedure described in step (iii) above in ethyl acetate (120 ml) 10% Pd—C (2.1 g) was subjected to hydrogenation at 50–60 psi of hydrogen pressure at room temperature for 30 h. The progress of the reaction was monitored by TLC. After completion of the reaction, the catalyst was filtered and the solvent was removed under reduced pressure to yield the title compound of the formula (13) (8.2 g, 95%).

Step-v:
Preparation of S(−)-ethyl 3-[4-[2-(phenoxazin-10-yl) ethoxy]phenyl]-2-ethoxypropionate of the Formula (16):

A mixture of the S(−)-ethyl 2-ethoxy-3-(4-hydroxyphenyl)propionate of the formula (13) (25 g) obtained according to the procedure described in step (iv) above, the mesylate of the formula (15) (32 g), potassium carbonate (36 g), and toluene (250 ml) was refluxed for a period of 15–20 hours. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title compound of the formula (16) (46–47 g, 98–99%), as an oily material.

Step-vi:
Preparation of S(−)-3-[4-[2-(phenoxazin-10-yl)ethoxy] phenyl]-2-ethoxypropanoic acid of the Formula (1):

To a mixture of S(−)-ethyl 3-[4-[2-(phenoxazin-10-yl) ethoxy]phenyl]-2-ethoxypropionate of the formula (16) (45 g) obtained according to the procedure described in step (v) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (16), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded the title compound of the formula (1) (38–39 g, 90–92%).

EXAMPLE 12

Step-i:
Preparation of (S2-amino-3-(4-benzyloxyphenyl)propionic acid of the Formula (22):

To a solution of L-tyrosine of the formula (21) (18.1 g) in 2N NaOH solution (115 ml), copper sulphate solution (12.5 g of $CuSO_4$ in 50 ml of water) was added and heated at 60° C. for 1.5 h. The reaction mixture was cooled to room temperature and methanol (350 ml) and 2N NaOH (12.5 ml) was added and then benzyl bromide (12 ml) was added drop wise. The reaction mass was allowed to warm to room temperature. The precipitate was filtered and washed to give the title compound as white to off-white solid (18.5 g, 66.8%) (Ref. Bodansky & Bodansky pp50).

Step-(ii):
Preparation of S(−)-2-hydroxy-3-(4-benzyloxyphenyl) propionic acid of the Formula (11'):

To a stirred solution of (S)-2-amino-3-(4-benzyloxyphenyl)propionic acid of the formula (22) (300 g) obtained according to the procedure described in step (i) above, in THF (1.81) and dilute $H_2SO_4$ (75 ml in 1.21 of $H_2O$) at 0° C., a solution of $NaNO_2$ (210 mg in 400 ml $H_2O$) was added slowly between 0° C. to 15° C. After complete addition of $NaNO_2$ the reaction mixture was maintained below 25° C. for a period of 3 h. The progress of the reaction was monitored by TLC. After completion of the reaction, the reaction mixture was extracted with cold chloroform or DCM. The organic extracts were concentrated and the residue was purified by washing with diisopropyl ether to give the title compound of the formula (11') as off white to yellowish solid (145 g, 48.3%).

Step-(iii):
Preparation of S(−)-ethyl 2-ethoxy-3-(4-benzyloxyphenyl)propionate of the Formula (12):

To a slurry of S(−)-2-hydroxy-3-(4-benzyloxyphenyl)propionic acid of the formula (11') (2 g), obtained according to the procedure described in step (ii) above $K_2CO_3$ (5.1 g) in toluene (20 ml), diethyl sulphate (2.8 g) was added and heated under reflux with dean-stark apparatus for 12 h. The progress of the reaction mixture was monitored by TLC After completion of the reaction, the reaction mixture was cooled and filtered and concentrated. The compound was purified by column chromatography to give the title compound of the formula (12) as faint yellow colored syrupy liquid, (1.23 g, 65%).

Step-iv:
Preparation of S(−)-ethyl 2-ethoxy-3-(4-hydroxyphenyl) propionate of the Formula (13):

A solution of S(−)-ethyl 2-ethoxy-3-(4-benzyloxyphenyl) propionate of the formula (12) (12 g) obtained according to the procedure described in step (iii) above in ethyl acetate (120 ml) 10% Pd—C (2.1 g) was subjected to hydrogenation at 50–60 psi of hydrogen pressure at room temperature for 30 h. The progress of the reaction was monitored by TLC. After completion of the reaction, the catalyst was filtered and the solvent was removed under reduced pressure to yield the title compound of the formula (13) (8.2 g, 95%).

Step-v:
Preparation of S(−)-ethyl 3-[4-[2-(phenoxazin-10-yl) ethoxy]phenyl]-2-ethoxypropionate of the Formula (16):

A mixture of S(−)-ethyl 2-ethoxy-3-(4-hydroxyphenyl) propionate of the formula (13) (25 g) obtained according to the procedure described in step (iv) above, the mesylate of the formula (15) (32 g), potassium carbonate (36 g) and toluene (250 ml) was refluxed for a period of 15–20 hours. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title compound of the formula (16) (46–47 g, 98–99%), as an oily material.

Step-vi:
Preparation of S(−)-3-[4-[2-(phenoxazin-10-yl)ethoxy] phenyl]-2-ethoxypropanoic acid of the Formula (1):

To a mixture of S(−)-ethyl 3-[4-[2-(phenoxazin-10-yl) ethoxy]phenyl]-2-ethoxypropionate of the formula (16) (45 g) obtained according to the procedure described in step (v) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (16), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded the title compound of the formula (1) (38–39 g, 90–92%).

EXAMPLE 13

Step-i:
Preparation of (S)-2-amino-3-(4-benzyloxyphenyl)propionic acid of the Formula (22):

To a solution of L-tyrosine of the formula (21) (18.1 g) in 2N NaOH solution (115 ml), copper sulphate solution (12.5 g of $CuSO_4$ in 50 ml of water) was added and heated at 60° C. for 1.5 h. The reaction mixture was cooled to room temperature and methanol (350 ml) and 2N NaOH (12.5 ml) was added and then benzyl bromide (12 ml) was added drop wise. The reaction mass was allowed to warm to room temperature. The precipitate was filtered and washed to give the title compound as white to off-white solid (18.5 g, 66.8%) (Ref. Bodansky & Bodansky pp50).

Step-(ii):
Preparation of S(−)-2-hydroxy-3-(4-benzyloxyphenyl) propionic acid of the Formula (11'):

To a stirred solution of (S)-2-amino-3-(4-benzyloxyphenyl)propionic acid of the formula (22) (300 g) obtained according to the procedure described in step (i) above, in THF (1.8 L) and dilute $H_2SO_4$ (75 ml in 1.2 L of $H_2O$) at 0° C., a solution of $NaNO_2$ (210 mg in 400 ml $H_2O$) was added slowly between 0° C. to 15° C. After complete addition of $NaNO_2$ the reaction mixture was maintained below 25° C. for a period of 3 h. The progress of the reaction was monitored by TLC. After completion of the reaction, the reaction mixture was extracted with cold chloroform or DCM. The organic extracts were concentrated and the residue was purified by washing with diisopropyl ether to give the title compound of the formula (11') as off white to yellowish solid (145 g, 48.3%).

Step-(iii):
Preparation of S(−)-ethyl 2-ethoxy-3-(4-benzyloxyphenyl)propionate of the Formula (12):

To a stirred solution of (S)-2-hydroxy-3-(4-benzyloxyphenyl)propionic acid of the formula (11') (5.0 g) obtained according to the procedure described in step (ii) above in methyl isobutyl ketone (30 ml) at room temperature, $K_2CO_3$ (25.0 g) and diethyl sulphate (7.07 g) was added and heated at reflux for 24 h. The progress of the reaction was monitored by TLC. After completion of the reaction, the reaction mixture was filtered and the filtrate concentrated. The solid thus obtained was extracted with ethyl acetate. The combined organic extracts were washed with water, dried and concentrated to afford the crude compound. The crude compound was purified by column chromatography to give the title compound of the formula (12) as syrupy liquid, (5.8 g, 87%).

Step-iv:
Preparation of S(−)-ethyl 2-ethoxy-3-(4-hydroxyphenyl) propionate of the Formula (13):

A solution of S(−)-ethyl 2-ethoxy-3-(4-benzyloxyphenyl) propionate of the formula (12) (12 g) obtained according to the procedure described in step (iii) above in ethyl acetate (120 ml) 10% Pd—C (2.1 g) was subjected to hydrogenation at 50–60 psi of hydrogen pressure at room temperature for 30 h. The progress of the reaction was monitored by TLC. After completion of the reaction, the catalyst was filtered and the solvent was removed under reduced pressure to yield the title compound of the formula (13) (8.2 g, 95%).

Step-v:
Preparation of S(−)-ethyl 3-[4-[2-(phenoxazin-10-yl) ethoxy]phenyl]-2-ethoxypropionate of the Formula (16):

A mixture of S(−)-ethyl 2-ethoxy-3-(4-hydroxyphenyl) propionate of the formula (13) (25 g) obtained according to the procedure described in step (iv) above, the mesylate of the formula (15) (32 g), potassium carbonate (36 g) and toluene (250 ml) was refluxed for a period of 15–20 hours. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title compound of the formula (16) (46–47 g, 98–99%), as an oily material.

Step-vi:

Preparation of S(−)-3-[4-[2-(phenoxazin-10-yl)ethoxy]phenyl]-2-ethoxypropanoic acid of the Formula (1):

To a mixture of S(−)-ethyl 3-[4-[2-(phenoxazin-10-yl)ethoxy]phenyl]-2-ethoxypropionate of the formula (16) (45 g) obtained according to the procedure described in step (v) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (16), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded the title compound of the formula (1) (38–39 g, 90–92%).

EXAMPLE 14

Step-i:

Preparation of (S)-2-amino-3-(4-benzyloxyphenyl)propionic acid of the Formula (22):

To a solution of L-tyrosine of the formula (21) (18.1 g) in 2N NaOH solution (115 ml), copper sulphate solution (12.5 g of $CuSO_4$ in 50 ml of water) was added and heated at 60° C. for 1.5 h. The reaction mixture was cooled to room temperature and methanol (350 ml) and 2N NaOH (12.5 ml) was added and then benzyl bromide (12 ml) was added drop wise. The reaction mass was allowed to warm to room temperature. The precipitate was filtered and washed to give the title compound as white to off-white solid (18.5 g, 66.8%) (Ref. *Bodansky & Bodansky* pp50).

Step-(ii):

Preparation of S(−)-2-hydroxy-3-(4-benzyloxyphenyl)propionic acid of the Formula (11'):

To a stirred solution of (S)-2-amino-3-(4-benzyloxyphenyl)propionic acid of the formula (22) (300 g) obtained according to the procedure described in step (i) above, in THF (1.8 L) and dilute $H_2SO_4$ (75 ml in 1.2 L of $H_2O$) at 0° C., a solution of $NANO_2$ (210 mg in 400 ml $H_2O$) was added slowly between 0° C. to 15° C. After complete addition of $NANO_2$ the reaction mixture was maintained below 25° C. for a period of 3 h. The progress of the reaction was monitored by TLC. After completion of the reaction, the reaction mixture was extracted with cold chloro-form or DCM. The organic extracts were concentrated and the residue was purified by washing with diisopropyl ether to give the title compound of the formula (11') as off white to yellowish solid (145 g, 48.3%).

Step-(iii):

Preparation of S(−)-ethyl 2-ethoxy-3-(4-benzyloxyphenyl)pronionate of the Formula (12):

To a stirred slurry of NaH (2.7 g) in THF (200 ml) at 0° C., a solution of S(−)-2-hydroxy-3-(4-benzyloxyphenyl)propionic acid of the formula (11') (10 g) obtained according to the procedure described in step (ii) above in THF (50 ml) was added slowly in about 30 min time followed by ethyl iodide (18.1 g) in about 1 h time and allowed to reach room temperature in about 2 h time. The progress of the reaction was monitored by TLC. After completion of the reaction, the reaction mixture was poured into ice cold water and the compound was extracted with toluene. The combined organic extracts were washed with water, dried and concentrated to give the title compound of the formula (12) faint brown colored syrupy liquid (11.2 g, 85.9 g).

Step-iv:

Preparation of S(−)-ethyl 2-ethoxy-3-(4-hydroxyphenyl)propionate of the Formula (13):

A solution of S(−)-ethyl 2-ethoxy-3-(4-benzyloxyphenyl)propionate of the formula (12) (12 g) obtained according to the procedure described in step (iii) above in ethyl acetate (120 ml) 10% Pd—C (2.1 g) was subjected to hydrogenation at 50–60 psi of hydrogen pressure at room temperature for 30 h. The progress of the reaction was monitored by TLC. After completion of the reaction, the catalyst was filtered and the solvent was removed under reduced pressure to yield the title compound of the formula (13) (8.2 g, 95%).

Step-v:

Preparation of S(−)-ethyl 3-[4-[2-(phenoxazin-10-yl)ethoxy]phenyl]-2-ethoxypropionate of the Formula (16):

A mixture of S(−)-ethyl 2-ethoxy-3-(4-hydroxyphenyl)propionate of the formula (13) (25 g) obtained according to the procedure described in step (iv) above the mesylate of the formula (15) (32 g), potassium carbonate (36 g) and toluene (p50 ml) was refluxed for a period of 15–20 hours. The progress of the reaction was monitored by TLC After completion of the reaction, the reaction mass was dumped into ice water and the toluene layer was separated while the aqueous layer was extracted with toluene. The combined organic extracts were washed with water and concentrated under vacuum to afford the title compound of the formula (16) (46–47 g, 98–99%), as an oily material.

Step-vi:

Preparation of S(−)-3-[4-[2-(phenoxazin-10-yl)ethoxy]phenyl]-2-ethoxypropanoic acid of the Formula (1):

To a mixture of S(−)-ethyl 3-[4-[2-(phenoxazin-10-yl)ethoxy]phenyl]-2-ethoxypropionate of the formula (16) (45 g) obtained according to the procedure described in step (v) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (16), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded the title compound of the formula (1) (38–39 g, 90–92%).

EXAMPLE 15

Step-i:

Preparation of 4-benzyloxybenzaldehyde of the Formula (8):

4-Hydroxybenzaldehyde of the formula (7) (100 g), potassium carbonate (226 g) and dimethylformamide (500 ml) were taken in a reaction flask and stirred for 15 minutes. Benzylchloride (114 g) was then added at room temperature and the reaction mass was stirred at the same temperature for a period of 8–10 h. The progress of the reaction was monitored with TLC. After completion of the reaction, the reaction mixture was dumped into ice water and extracted with toluene The combined organic extracts were washed with 10% aq. sodium hydroxide solution followed bar, water. The solvent was removed under reduced pressure and the resulting residue was triturated with pet. ether to afford the title compound of the formula (8) (160–165 g, 93–95%).

Step-ii:

Preparation of ethyl-2,3-epoxy-3-(4-benzyloxyphenyl) propionate of the Formula (9):

4-Benzyloxybenzaldehyde of the formula (8) (100 g) obtained according to the procedure described in step (i) above, was added to a solution of sodium ethoxide (64 g) in absolute ethanol followed by the addition of ethylchloroacetate (87 g) over a period of 30–45 minutes, maintaining ambient temperature. The reaction mixture was stirred at the same temperature for 3–5 h. The progress of the reaction was monitored with TLC. After completion of the reaction, the reaction mixture was dumped into ice water and stirred for 5–10 minutes. The solid thus obtained was filtered, washed with water and dried to afford the title compound of the formula (9) (126–129 g, 90–92%).

Step-iii:

Preparation of racemic ethyl 2-hydroxy-3-(4-benzyloxyphenyl)propionate of the Formula (10):

A mixture of ethyl-2,3-epoxy-3-(4-benzyloxyphenyl)propionate of the formula (9) (125 g) obtained according to the procedure described in step (ii) above, 5% Pd/C catalyst (12.5 g) and 1,4-dioxane (750 ml) was hydrogenated at room temperature at 5–10 psi of hydrogen pressure for a period of 10–15 h. The progress of the reaction was monitored by TLC. After completion of the reaction, the catalyst was filtered and the solvent was removed under reduced pressure to afford the title compound of the formula (10) (100–105 g, 80–83%).

Step-iv:

Preparation of S(−)-2-hydroxy-3-(4-benzyloxyphenyl) propionic acid of the Formula (11):

A mixture of racemic ethyl 2-hydroxy-3-(4-benzyloxyphenyl)propionate of the formula (10) (100 g) obtained according to the procedure described in step (iii) above and 10% aq. sodium hydroxide solution (500 ml) was stirred at room temperature for a period of 1–2 h The progress of the reaction was monitored by TLC. After completion of the reaction, the reaction mixture was acidified with dil. hydrochloric acid at 15–20° C. and the solid thus obtained was filtered and washed with water to afford racemic 2-hydroxy acid (72–77 g, 80–85%).

To a solution of racemic 2-hydroxy-3-(4-benzyloxyphenyl)propionic acid (75 g) obtained according to the procedure described above in ethylacetate (1.1 L) was added R(+)-α-methylbenzylamine (33 g) and the mixture was stirred at room temperature for a period of 2–4 h. The solid thus obtained was filtered and the acid was regenerated after acidification to afford S(−)-2-hydroxy-3-(4-benzyloxyphenyl)propionic acid of the formula (11), (33–35 g, 44–47%).

The R(+)-α-hydroxy acid obtained from the mother liquor was racemized and mixed with subsequent batches for resolution. The overall yield obtained by several such reprocesses was ~90–95%.

Step-v:

Preparation of S(−)-ethyl 2-ethoxy-3-(4-benzyloxyphenyl)propionate of the Formula (12):

To a slurry of sodium hydride (60% suspension in oil, 13 g) and dimethyl formamide (70 ml) was added a solution of S(−)-2-hydroxy-3-(4-benzyloxyphenyl)propionic acid of the formula (11) (35 g) obtained according to the procedure described in step (iv) above, in dimethylformamide (105 ml) at 5–10° C. over a period of 15–30 minutes. The temperature was allowed to attain room temperature and maintained at the same temperature for 1–3 hours. Ethyl iodide (62 g) was added slowly by maintaining the temperature at 25–30° C. over a period of 2–3 hours. The progress of the reaction was monitored by TLC. After completion of the reaction, the reaction mixture was dumped into ice water and extracted with toluene. The combined organic extracts were washed with water and the solvent was removed under reduced pressure to afford the title compound of the formula (12) (41–42 g, 98–99%).

Step-vi:

Preparation of S(−)-ethyl 2-ethoxy-3-(4-hydroxyphenyl) propionate of the Formula (13):

A mixture of S(−)-ethyl 2-ethoxy-3-(4-benzyloxyphenyl) propionate of the formula (12) (40 g) obtained according to the procedure described in step (v) above, 5% Pd/C catalyst (8 g) and tetrahydrofuran (120 ml) was subjected to hydrogenation at room temperature and 50–60 psi of hydrogen pressure for a period of 8–12 hours. The progress of the reaction was monitored by TLC. After completion of the reaction, the catalyst was filtered off and the solvent was removed under reduced pressure to afford debenzylated compound of the formula (13) (28–29 g, 97–98%).

Step-vii:

Preparation of S(−)-ethyl 2-ethoxy-3-(3-iodo-4-hydroxyphenyl)propionate of the Formula (14):

To stirred solution of S(−)-ethyl 2-ethoxy-3-(4-hydroxyphenyl)propionate of the formula (13) (20 g) obtained according to the procedure described in step (vi) above and dimineralised water (100 ml), ICl (13.6 g, 4.4 ml) in HCl (80 ml) was added dropwise at room temperature for 30 min. The reaction mixture was heated to 75° C. to 80° C. for 20 h. The progress of the reaction was monitored by TLC. After completion of the reaction, toluene (200 ml) was added to the reaction mixture and extracted with dimineralised water. Organic extracts were concentrated to yield the crude compound. The crude compound was purified by column chromatography using 3% ethyl acetate in pet. ether to yield the title compound (10.3 g, 98.13%).

Step-viii:

Preparation of S(−)-ethyl 3-[3-iodo-4-[2-(phenoxazin-10-yl)ethoxy]phenyl]-2-ethoxypropionate of the Formula (16):

A mixture of S(−)-ethyl 2-ethoxy-3-(3-iodo-4-hydroxyphenyl)propionate of the formula (14) (25 g) obtained according to the procedure described in step (vii) above, the mesylate of the formula (15) (32 g), potassium carbonate (36 g) and toluene (250 ml) was refluxed for a period of 15–20 hours. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title compound of the formula (16) (46–47 g, 98–99%), as an oily material.

Step-ix:

Preparation of S(−)-3-[3-iodo-4-[2-(phenoxazin-10-yl) ethoxy]phenyl]-2-ethoxypropanoic acid of the Formula (1):

To a mixture of S(−)-ethyl 3-[3-iodo-4-[2-(phenoxazin-10-yl)ethoxy]phenyl]-2-ethoxypropionate of the formula (16) (45 g) obtained according to the procedure described in step (viii) above and methanol (225 ml) was added aqueous 10% sodium hydroxide solution (225 ml) slowly at room temperature over a period of 10–15 minutes. The reaction mixture was stirred at the same temperature for a period of 2–4 h. The progress of the reaction was monitored by TLC. After the complete hydrolysis of the compound of the formula (16), the reaction mass was diluted with water (225 ml) and washed with toluene to remove the impurities. The aqueous layer was acidified with dilute hydrochloric acid and extracted with toluene. Combined organic extracts were washed with water and concentrated under reduced pressure to half the volume and treated with activated charcoal. Filtration of the charcoal followed by concentration of toluene to ~50 ml and precipitation with pet. ether afforded the title compound of the formula (1) (38–39 g, 90–92%).

EXAMPLE 16

Step-i:

Preparation of 4-benzyloxybenzaldehyde of the Formula (8):

4-Hydroxybenzaldehyde of the formula (7) (100 g), potassium carbonate (226 g) and dimethylformamide (500 ml) were taken in a reaction flask and stirred for 15 minutes. Benzylchloride (114 g) was then added at room temperature and the reaction mass was stirred at the same temperature for a period of 8–10 h. The progress of the reaction was monitored by TLC. After completion of the reaction, the reaction mixture was dumped into ice water and extracted with toluene. The combined organic extracts were washed with 10% aq. sodium hydroxide solution followed by water. The solvent was removed under reduced pressure and the resulting residue was triturated with pet. ether to afford the title compound of the formula (8) (160–165 g, 93–95%).

Step-ii:

Preparation of ethyl-2,3-epoxy-3-(4-benzyloxyphenyl) propionate of the Formula (9):

4-Benzyloxybenzaldehyde of the formula (3) (100 g) obtained according to the procedure described in step (i) above was added to a solution of sodium ethoxide (64 g) in absolute ethanol followed by the addition of ethylchloroacetate (87 g) over a period of 30–45 minutes, maintaining ambient temperature. The reaction mixture was stirred at the same temperature for 3–5 h. The progress of the reaction was monitored by TLC. After completion of the reaction, the reaction mixture was dumped into ice water and stirred for 5–10 minutes. The solid thus obtained was filtered, washed with water and dried to afford the title compound of the formula (9) (126–129 g, 90–92%).

Step-iii:

Preparation of racemic ethyl 2-hydroxy-3-(4-benzyloxyphenyl)propionate of the Formula (10):

A mixture of ethyl-2,3-epoxy-3-(4-benzyloxyphenyl)propionate of the formula (9) (125 g) obtained according to the procedure described in step (ii) above, 5% Pd/C catalyst (12.5 g) and 1,4-dioxane (750 ml) was hydrogenated at room temperature at 5–10 psi of hydrogen pressure for a period of 10–15 h The progress of the reaction was monitored by TLC. After completion of the reaction, the catalyst was filtered and the solvent was removed under reduced pressure to afford the title compound of the formula (10) (100–105 g, 80–83%).

Step-iv:

Preparation of racemic ethyl 2-ethoxy-3-(4-benzyloxyphenyl)propionate of the Formula (12a):

To a slurry of sodium hydride (60% suspension in oil, 7.5 g) and dimethyl formamide (70 ml) was added a solution of the racemic ethyl 2-hydroxy-3-(4-benzyloxyphenyl)propionate of the formula (10) (40 g) obtained according to the procedure described in step (iii) above in dimethylformamide (105 ml) at 5–10° C. over a period of 15–30 minutes. The temperature was allowed to attain room temperature and maintained at the same temperature for 1–3 h. Ethyl iodide (36 g) was added slowly by maintaining the temperature at 25–30° C. over a period of 2–3 hours. The progress of the reaction was monitored by TLC. After completion of the reaction, the reaction mixture was dumped into ice water and extracted with toluene. The combined organic extracts were washed with water and the solvent was removed under reduced pressure to afford title compound of the formula (12a) (47–48 g, 98–99%).

Step-v:

Preparation of racemic ethyl 2-ethoxy-3-(4-hydroxyphenyl)propionate of the Formula (13a):

A mixture of racemic ethyl 2-ethoxy-3-(4-benzyloxyphenyl)propionate of the formula (12a) (40 g) obtained according to the procedure described in step (iv) above, 5% Pd/C catalyst (8 g) and tetrahydrofuran (120 ml) was subjected to hydrogenation at room temperature and 50–60 psi-of hydrogen-pressure for a period of 8–12 h. The progress of the reaction was monitored by TLC. After completion of the reaction, the catalyst was filtered off and the solvent was removed under reduced pressure to afford the title compound of the formula (13a) (28–29 g, 97–98%).

Step-vi:

Preparation of racemic ethyl 2-ethoxy-3-(3-iodo-4-hydroxyphenyl) propionate of the Formula (14a):

To stirred solution of racemic ethyl 2-ethoxy-3-(4-hydroxyphenyl)propionate of the formula (13a) (20 g) obtained according to the procedure described in step (v) above and dimineralised water (100 ml), ICl (13.6 g, 4.4 ml) in HCl (80 ml) was added dropwise at room temperature for 30 min. The reaction mixture was heated to 75° C. to 80° C. for 20 h. The progress of the reaction was monitored by TLC. After completion of the reaction, toluene (200 ml) was added to the reaction mixture and extracted with dimineralised water. Organic extracts were concentrated to yield the crude compound. The crude compound was purified by column chromatography using 3% ethyl acetate in pet ether to yield the title compound (10.3 g, 98.13%)

Step-vii:

Preparation of racemic ethyl 3-[3-iodo-4-[2-(phenoxazin-10-yl)ethoxy]phenyl]-2-ethoxypropionate of the Formula (4):

A mixture of racemic ethyl 2-ethoxy-3-(iodo-4-hydroxyphenyl)propionate of the formula (13a) (25 g) obtained according to the procedure described in step (vi) above, the mesylate of the formula (15) (32 g), potassium carbonate (36 g) and toluene (250 ml) was refluxed for a period of 15–20 h. The progress of the reaction was monitored by TLC. After completion of the reaction, the reaction mass was dumped into ice water and the toluene layer was separated while the aqueous layer was extracted with toluene. The combined organic extracts were washed with water and concentrated under vacuum to afford the title of the formula (4) (46–47 g, 98–99%) as an oily material.

Step-viii:

Preparation of racemic 3-[3-iodo-4-[2-(phenoxazin-10-yl)ethoxy]phenyl]-2-ethoxypropanoic acid of the Formula (5):

To a mixture of racemic ethyl 3-[3-iodo-4-[2-(phenoxazin-10-yl)ethoxy]phenyl]-2-ethoxypropionate of the formula (4) (45 g) obtained according to the procedure described in step (vii) above and methanol (225 ml), was added aqueous 10% sodium hydroxide solution (225 ml) slowly at room temperature over a period of 10–15 minutes. The reaction mixture was stirred at the same temperature for a period of 2–4 h The progress of the reaction was monitored by TLC. After the complete hydrolysis of the compound of the formula (4), the reaction mass was diluted with water (225 ml) and washed with toluene to remove the impurities. The aqueous layer was acidified with dilute hydrochloric acid and extracted with toluene. Combined toluene extracts were washed with water and concentrated under reduced pressure to half the volume and treated with activated charcoal. Filtration of the charcoal followed by concentration of toluene to ~50 ml and precipitation with pet ether afforded racemic acid of the formula (5) as an off-white to white solid, which was filtered and dried at room temperature (~30° C.), (38–39 g, 90–92%).

Step-ix:

Preparation of S(−)-3-[3-iodo-4-[2-(phenoxazin-10-yl)ethoxy]phenyl]-2-ethoxypropanoic acid of the Formula (1):

To a solution of racemic 3-[4-[2-(phenoxazin-10-yl)ethoxy]phenyl]-2-ethoxypropanoic acid of the formula (5) (35 g) obtained according to the procedure described in step (viii) above in ethylacetate (525 ml) was added R(+)-α-methylbenzylamine (10 g) and the mixture was stirred at room temperature for a period of 2–4 h. The solid thus obtained was filtered and the acid was regenerated after acidification to afford (15–17 g, 44–47%) of S(−)-α-ethoxy acid of the formula (1). The R(+)-α-ethoxy acid obtained from the mother liquor was racemised and mixed with subsequent batches for resolution. The overall yield obtained by several such reprocesses was ~90–95%.

EXAMPLE 17

Step-i:

Preparation of (S)-2-amino-3-(4-benzyloxyphenyl)propionic acid of the Formula (22):

To a solution of L-tyrosine of the formula (21) (18.1 g) in 2N NaOH solution (115 ml), copper sulphate solution (12.5 g of $CuSO_4$ in 50 ml of water) was added and heated at 60° C. for 1.5 h. The reaction mixture was cooled to room temperature and methanol (350 ml) and 2N NaOH (12.5 ml) was added and then benzyl bromide (12 ml) was added drop wise. The reaction mass was allowed to warm to room temperature. The precipitate was filtered and washed to give the title compound as white to off-white solid (18.5 g, 66.8%) (Ref. *Bodansky & Bodansy* pp50).

Step-(ii):

Preparation of S(−)-2-hydroxy-3-(4-benzyloxyphenyl)propionic acid of the Formula (11'):

To a stirred solution of (S)-2-amino-3-(4-benzyloxyphenyl)propionic acid of the formula (22) (300 g) obtained according to the procedure described in step (i) above, in (1.81) and dilute $H_2SO_4$ (75 ml in 1.21 of $H_2O$) at 0° C., a solution of $NaNO_2$ (210 mg in 400 ml $H_2O$) was added slowly between 0° C. to 15° C. After complete addition of NaNO. the reaction mixture was maintained below 25° C. for a period of 3 h. The progress of the reaction was monitored by TLC. After completion of the reaction, the reaction mixture was extracted with cold chloroform or DCM. The organic extracts were concentrated and the residue was purified by washing with diisopropyl ether to give the title compound of the formula (11') as off white to yellowish solid (145 g, 48.3%).

Step-iii:

Preparation of S(−)-ethyl 2-hydroxy-3-(4-benzyloxyphenyl)propionate of the Formula (12):

To a slurry of potassium carbonate (25 g) in acetone, 2-hydroxy-3-(4-benzyloxyphenyl) propionic acid of the formula (11') (10 g) obtained according to the procedure described in step (ii) above was added and heated to reflux. After five minutes diethylsulphate (6.8 ml) was added drop wise and refluxed for further 24 h. The progress of the reaction was monitored by TLC. After completion of the reaction, potassium carbonate was filtered and the reaction mixture was washed with acetone. The combined filtrate and washings were evaporated to a reddish brown residue. The residue was diluted with ethyl acetate. The organic extracts were washed with water, dried over anhydrous sodium sulfate, concentrated to yield the title compound as a reddish brown oil (9.37 g, 85%).

Step-iv:

Preparation of S(−)-ethyl 2-hydroxy-3-(4-hydroxyphenyl)propionate of the Formula (13):

A solution of S(−)-ethyl 2-hydroxy-3-(4-benzyloxyphenyl)propionate of the formula (12) (7 g) obtained according to the procedure described in step (iii) above, in THF (35 ml) was hydrogenated over 5% Pd—C (3 g) at 50–60 psi of hydrogen pressure for 48 h at room temperature. The progress of the reaction was monitored by TLC. After completion of the reaction, the catalyst was filtered off and the filtrate was concentrated to yield the debenzylated compound of the formula (13) (4.41 g, 90%).

Step-v:

Preparation of S(−)-ethyl 3-[4-[2-(phenoxazin-10-yl)ethoxy]phenyl]-2-hydroxypropionate of the Formula (16):

To a solution of ethyl 2-hydroxy-3-(4-hydroxyphenyl)propionate of the formula (13) (4 g) obtained according to the procedure described in step (iv) above in toluene (40 ml), potassium carbonate (6.6 g) was added at room temperature and heated at reflux. Mesylate of the formula (15) (6.1) in toluene (40 ml) was added and refluxed for 38 h. The progress of the reaction was monitored by TLC. After completion of the reaction, the reaction mass was poured into cold water and extracted with toluene. The organic layer was concentrated to give the title compound as a light yellow oil (6.3 g, 80%)

Step-vi:

Preparation of S(−)-3-[4-[2-(phenoxazin-10-yl)ethoxy]phenyl]-2-hydroxy propionic acid of the Formula (1):

To a solution of S(−)-ethyl 3-[4-[2-(phenoxazin-10-yl)ethoxy]phenyl]-2-hydroxypropionate of the formula (16) (2.8 g) obtained according to the procedure described in step (v) above in methanol (30 ml), methanolic sodium hydroxide solution (2 g sodium hydroxide in 30 ml methanol) was added at room temperature and stirred for 5 h. The progress of the reaction was monitored by TLC. After completion of the reaction, methanol was stripped off. The residue was diluted with water and extracted with toluene. The aqueous layer was acidified with dilute hydrochloric acid and extracted with ethyl acetate. The combined organic extracts were washed with water, concentrated to yield the title compound as a semisolid residue (2.1 g, 80%). The compound was purified by column chromatography.

EXAMPLE 18

Step-i:

Preparation of (S)-2-amino-3-(4-benzyloxyphenyl)propionic acid of the Formula (22):

To a solution of L-tyrosine of the formula (21) (18.1 g) in 2N NaOH solution (115 ml), copper sulphate solution (12.5 g of $CuSO_4$ in 50 ml of water) was added and heated at 60° C. for 1.5 h. The reaction mixture was cooled to room temperature and methanol (350 ml) and 2N NaOH (12.5 ml) was added and then benzyl bromide (12 ml) was added drop wise. The reaction mass was allowed to warm to room temperature. The precipitate was filtered and washed to give the title compound as white to off-white solid (18.5 g, 66.8%) (Ref Bodansky & Bodanshy pp50).

Step-(ii):

Preparation of S(-)-2-hydroxy-3-(4-benzyloxyphenyl)propionic acid of the Formula (11'):

To a stirred solution of (S)-2-amino-3-(4-benzyloxyphenyl)propionic acid of the formula (22) (300 g) obtained according to the procedure described in step (i) above, in THF (1.8 L) and dilute $H_2SO_4$ (75 ml in 1.2 L of $H_2O$) at 0° C., a solution of $NaNO_2$ (210 mg in 400 ml $H_2O$) was added slowly between 0° C. to 15° C. After complete addition of $NaNO_2$ the reaction mixture was maintained below 25° C. for a period of 3 h. The progress of the reaction was monitored by TLC. After completion of the reaction, the reaction mixture was extracted with cold chloroform or DCM. The organic extracts were concentrated and the residue was purified by washing with diisopropyl ether to give the title compound of the formula (11') as off white to yellowish solid (145 g, 48.3%).

Step-iii:

Preparation of S(-)-methyl 2-methoxy-3-(4-benzyloxyphenyl)propionate of the Formula (12):

To a stirred slurry of sodium hydride (4 g) in DMF (100 ml) at 10–15° C., a solution of S(-)-2-hydroxy-3-(4-benzyloxyphenyl)propionic acid of the formula (11') (10 g) obtained according to the procedure described in step (ii) above in DMF (50 ml) was added and stirred at 0–5° C. for 30 minutes. Methyl iodide (20.8 g) was then added slowly at 15–20° C. and stirred for further 12 h. The progress of the reaction was monitored by TLC. After completion of the reaction, ice was added to the reaction mixture and extracted with toluene. The combined organic extracts were washed with water, brine and concentrated to yield the title compound as a reddish brown oil. (9.37 g, 85%).

Step-iv:

Preparation of S(-)-methyl 2-methoxy-3-(4-hydroxyphenyl)propionate of the Formula (13):

A solution of S(-)-methyl 2-methoxy-3-(4-benzyloxyphenyl)propionate of the formula (12) (7 g) obtained according to the procedure given in step (iii) above in THF (30 ml) was hydrogenated over 5% Pd—C at 50–60 psi of hydrogenation pressure at room temperature for 48 h. The progress of the reaction was monitored by TLC. After completion of the reaction, the catalyst was filtered off and the filtrate was concentrated to yield the debenzylated compound of the formula (13) (4.4 g, 90%). The product was purified by column chromatography.

Step-v:

Preparation of S(-)-methyl 3-[4-[2-(phenoxazin-10-yl)ethoxy]phenyl]-2-methoxypropionate of the Formula (16):

To a solution of S(-)-methyl 2-methoxy-3-(4-hydroxyphenyl)propionate of the formula (13) (4 g) obtained according to the procedure described in step (iv) above in toluene (40 ml), potassium carbonate (6.6 g) was added and heated to reflux. Solution of mesylate of the formula (15) (6.5 g) in toluene (20 ml) was added and continued reflux for further 38 h. The progress of the reaction was monitored by TLC. After completion of the reaction, the reaction mixture was poured into cold water and extracted with toluene. The combined organic extracts were washed with water and concentrated to give the title compound as a light yellow oil (7 g, 88.6%). The compound was purified by column chromatography.

Step-vi:

Preparation of S(-)-2-methoxy-3-[4-[2-(phenoxazin-10-yl)methoxy]phenyl]propionic acid of the Formula (1):

To a stirred solution of S(-)-methyl 3-[4-[2-(phenoxazin-10-yl)ethoxy]phenyl]-2-methoxypropionate of the formula (16) (7 g) obtained according to the procedure in step (v) above, in methanol (30 ml), 10% methanolic sodium hydroxide solution (40 ml) was added at room temperature and stirred for further 8. The progress of the reaction was monitored by TLC. After completion of the reaction, methanol was stripped off. The residue was diluted with water, extracted with toluene. The aqueous layer was acidified with dilute hydrochloric acid and the compound was extracted with ethyl acetate. The combined organic extracts were washed with water, dried over anhydrous sodium sulfate and concentrated to yield the title compound as a light pink solid residue (5.4 g, 80%). The compound was purified by column chromatography.

ADVANTAGES OF THE PRESENT PROCESS

A convergent synthesis of compound of the formula (1), has been developed which is commercially viable, simple and efficient with safe operations even in scale-up reactions.

The resolution is carried out at an early stage on the intermediate of the formula (10), instead of resolving at the final stage.

However, in the event of a small amount of racemization, if any, during the course of converting the intermediate compound of the formula (1) or the compound of the formula (14) to the final compound of the formula (1), resolution can easily be done employing for example chiral amines without losing much of the compound.

The overall yield of the process has been improved to ~25% and the time cycle required for the production of the compound of the formula (1) has been reduced drastically, which makes the process commercially very attractive.

Wherever possible resolution has been avoided thereby reducing the number of steps and loss of compound.

The invention claimed is:

1. A compound of formula 14

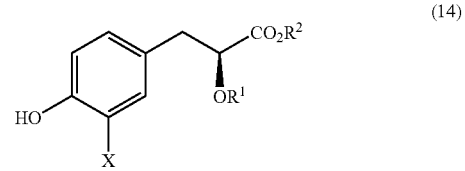

(14)

wherein $R^1$ represents hydrogen or lower alkyl group, $R^2$ represents lower alkyl group and X represents a halogen atom.

2. A compound according to claim 1, wherein $R^1$ is $C_1$–$C_6$ alkyl.

3. A compound according to claim 1, wherein $R^2$ is $C_1$–$C_6$ alkyl.

* * * * *

UNITED STATES PATENT AND TRADEMARK OFFICE
CERTIFICATE OF CORRECTION

| | | |
|---|---|---|
| PATENT NO. | : 7,223,881 B2 | Page 1 of 1 |
| APPLICATION NO. | : 10/325176 | |
| DATED | : May 29, 2007 | |
| INVENTOR(S) | : Mahender Rao Siripragada et al. | |

It is certified that error appears in the above-identified patent and that said Letters Patent is hereby corrected as shown below:

On title page, insert -- (63) Division of application No. 09/786,599, filed on May 30, 2001, which is a 371 of PCT/IB99/00684 filed on Apr. 16, 1999, which claims the benefit of application No. 60/127,228 filed on March 31, 1999 -- and item 30, after "1998" insert -- Oct. 29, 1998 (IN) ... 2342/MAS/1998 Oct. 29, 1998 (IN) ... 2341/MAS/1998 --.

Col. 1, line 4, before "FIELD" insert -- This application is a divisional of copending application application number 09/786,599 filed on MAY 30,2001, which is International Application PCT/IB99/00684 filed on April 16, 1999, which designated the U.S., claims the benefit thereof and incorporates the same by reference. The nonprovisional application designated above, namely application 09/786,599, filed MAY 30, 2001, claims the benefit of U.S. Provisional APPLICATION NO.: 60/127,228 FILING DATE MARCH 31, 1999 and incorporates the same by reference. --

Signed and Sealed this

Twentieth Day of November, 2007

JON W. DUDAS
*Director of the United States Patent and Trademark Office*